United States Patent
Hooper et al.

(10) Patent No.: US 6,562,376 B2
(45) Date of Patent: May 13, 2003

(54) DNA VACCINES AGAINST POXVIRUSES

(75) Inventors: Jay W. Hooper, New Market, MD (US); Alan L. Schmaljohn, Frederick, MD (US); Connie S. Schmaljohn, Frederick, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 133 days.

(21) Appl. No.: 09/800,632

(22) Filed: Mar. 7, 2001

(65) Prior Publication Data

US 2002/0176871 A1 Nov. 28, 2002

Related U.S. Application Data

(60) Provisional application No. 60/187,608, filed on Mar. 7, 2000.

(51) Int. Cl.$^7$ .................. A61K 9/14; A61K 31/711; A61K 39/275; C12N 15/86
(52) U.S. Cl. ............. 424/489; 424/199.1; 514/44; 435/459; 435/320.1; 435/235.1
(58) Field of Search ............... 514/44; 424/186.1, 424/232.1, 400, 199.1, 489; 536/23.72; 435/459, 320.1, 235.1

(56) References Cited

PUBLICATIONS

Moss, B. "Poxviridae: The viruses and their replication." In Fields Virology, Third edition, ed. B.N. Fields et al, Llppincott–Raven Publishers, Philadelphia. 1996. pp. 2637–2671.*

Fenner, F. "Poxviruses." In Fields Virology, Third edition, ed. B.N. Fields et al, Llppincott–Raven Publishers, Philadelphia. 1996. Pp. 2673–2702.*

Hooper et al (Virology 266:329–339, Jan. 2000).*

Galmiche et al (Virology 254:71–80, Feb. 1999).*

Mercer et al (Veterinary Microbiology 41:373–82, 1994) Abstract only cited.*

Yirrell et al (British Journal of Dermatology 130:438–43, 1994) Abstract only cited.*

Mercer et al (Virology 229:193–200, 1997).*

International Search Report for parallel international application PCT/US01/07391, dated Sep. 18, 2001, 3 pages.

Hooper et al., "DNA Vaccination with Vaccinia Virus L1R and A33R Genes Protects MIce Against a Lethal Poxvirus Challenge.", Virology 266, pp. 329–339 (2000).

Vazquez and Esteban, "Identification of Functional Domains in the 14–Kilodalton Envelope Protein (A27L) of Vaccinia Virus", J. Virology, vol. 73, No. 11, Nov. 1999, pp. 9098–9109.

Herrera et al., "Functinal Analysis of Vaccinia Virus B5R Protein: Essential Role in Virus Envelopment is Independent of a Large Portion of the Extracellular Domain", J. Virology, vol. 72, No. 1, Jan. 1998, pp. 294–302.

* cited by examiner

*Primary Examiner*—Mary E. Mosher
(74) *Attorney, Agent, or Firm*—Elizabeth Arwine

(57) ABSTRACT

In this application is described a poxvirus naked DNA vaccine which protects animals against poxvirus challenge comprising IMV and EEV nucleic acids from poxvirus. Methods of use of the vaccine and its advantages are described.

19 Claims, 13 Drawing Sheets

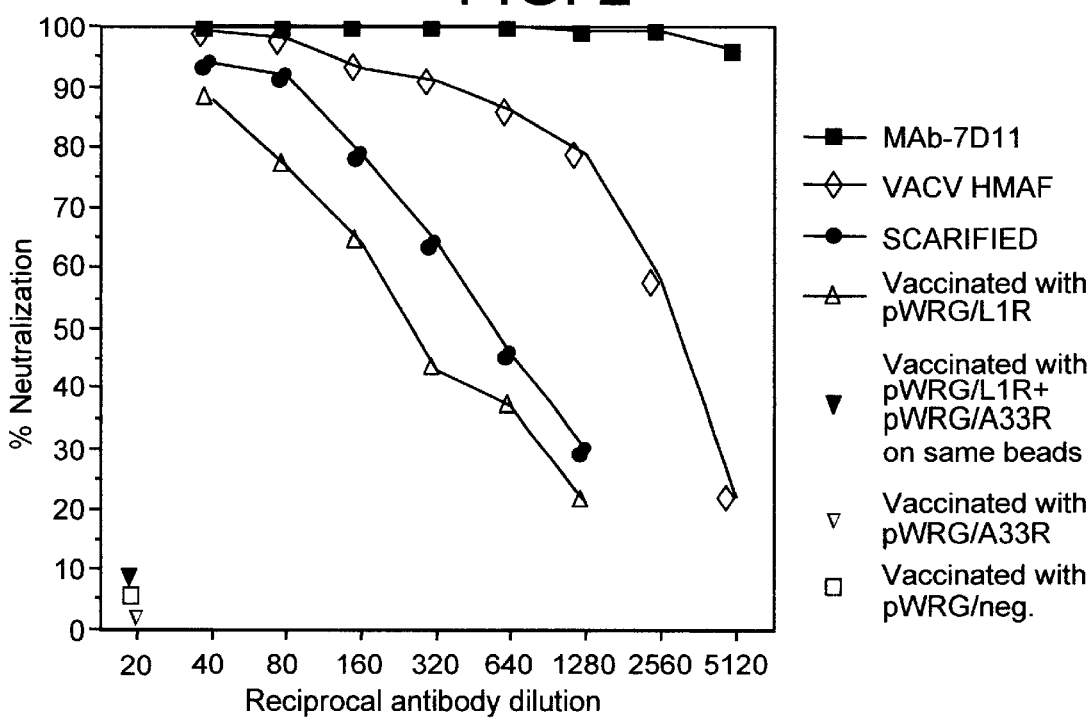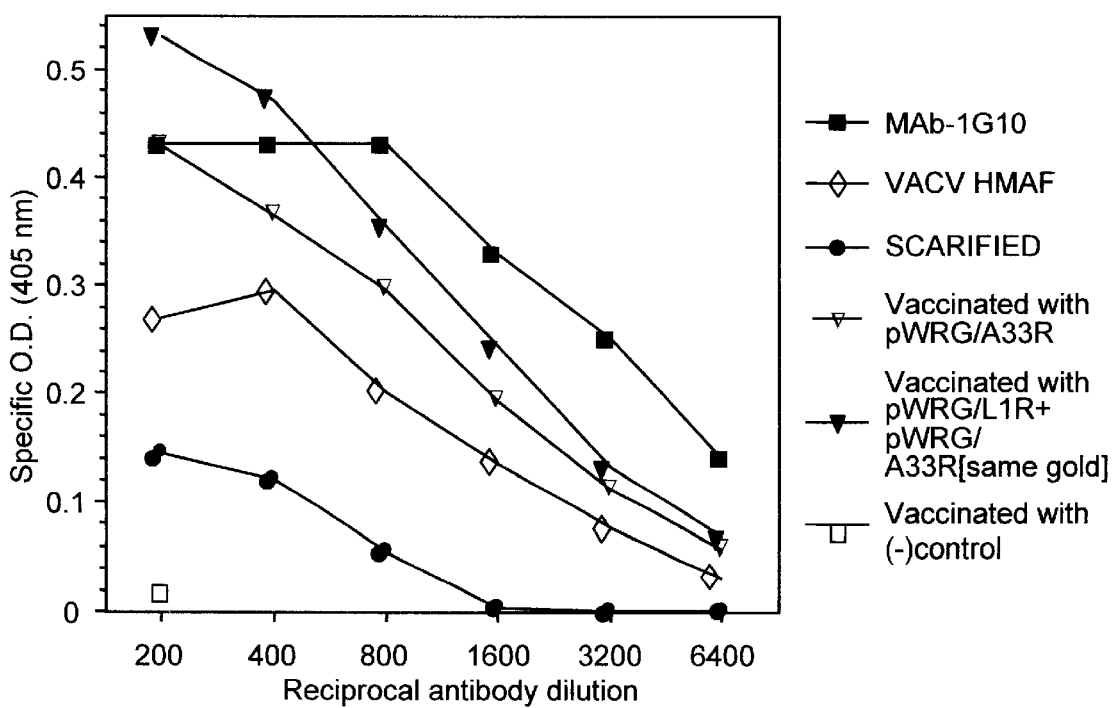

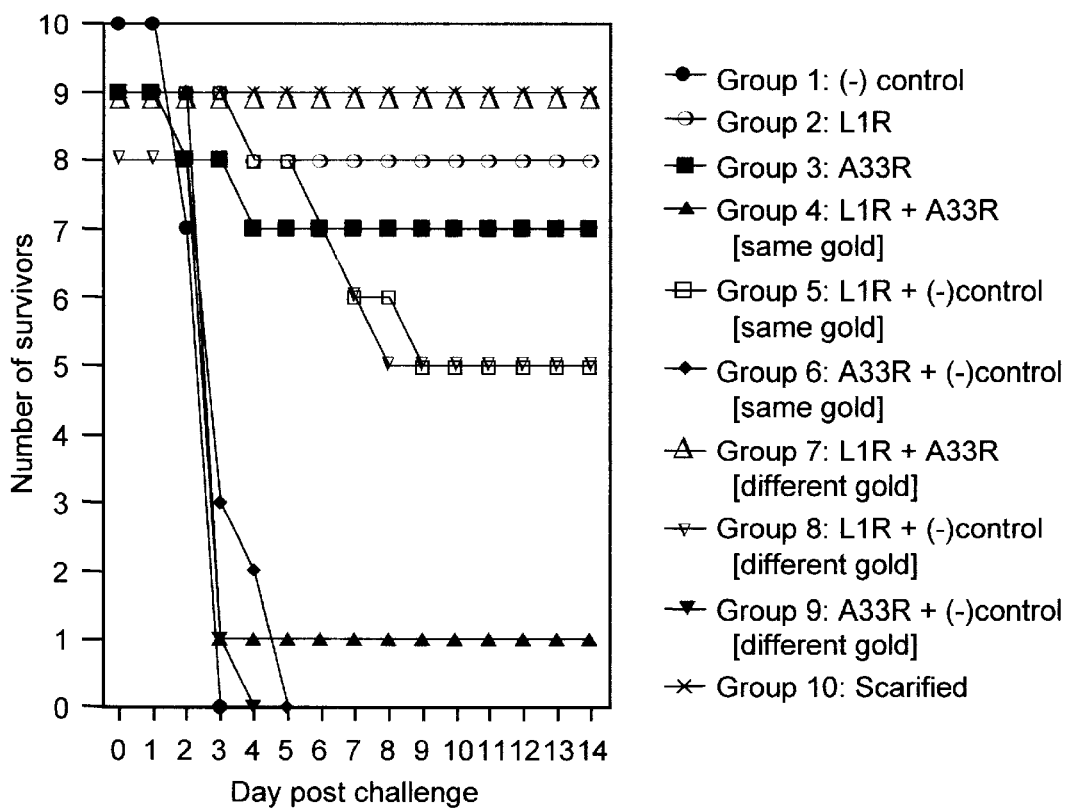
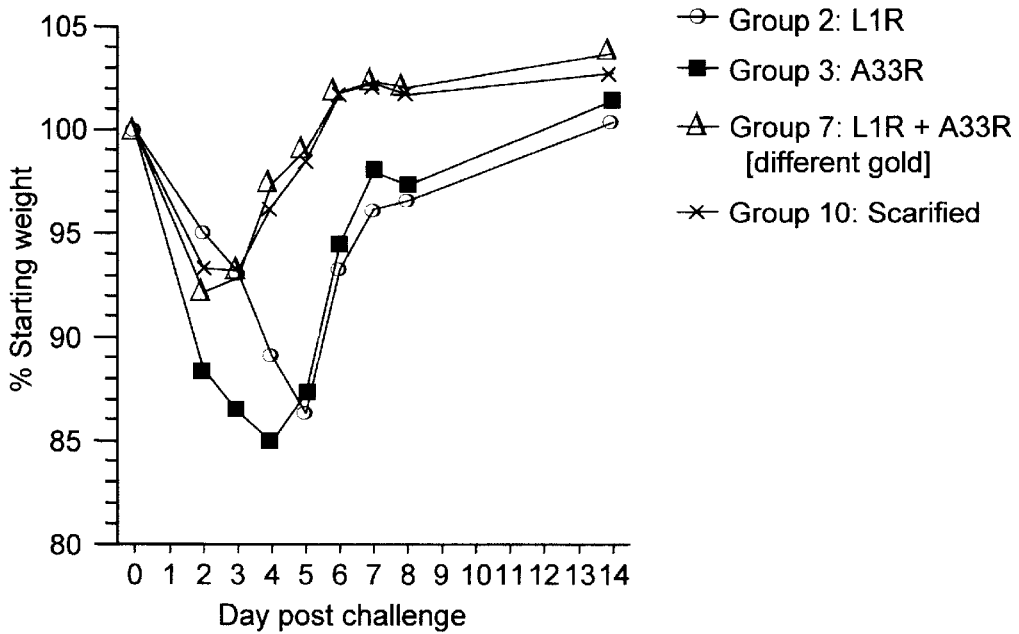

A27L | DRQE D E / EAAG N D | 110aa — 94.5%

A33R | L DK LTA I S / I D KQ FAT T T | 185aa — 95.1%

L1R | R M / K I | 250aa — 99.2%

B5R | NQH STMSNG PEY S V D P / KSY AI I IKD SDH T I N D | 317aa — 95.0%

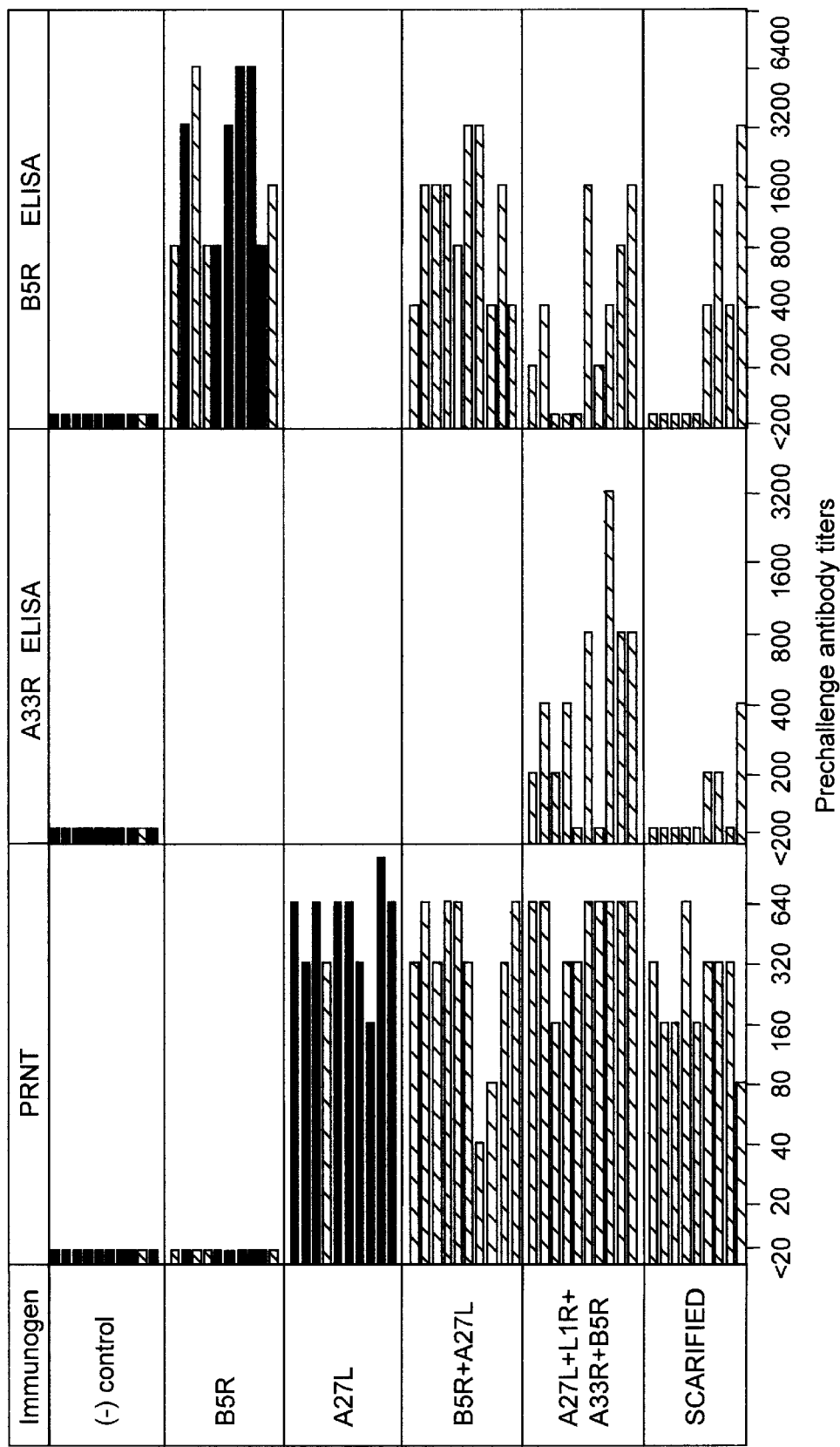

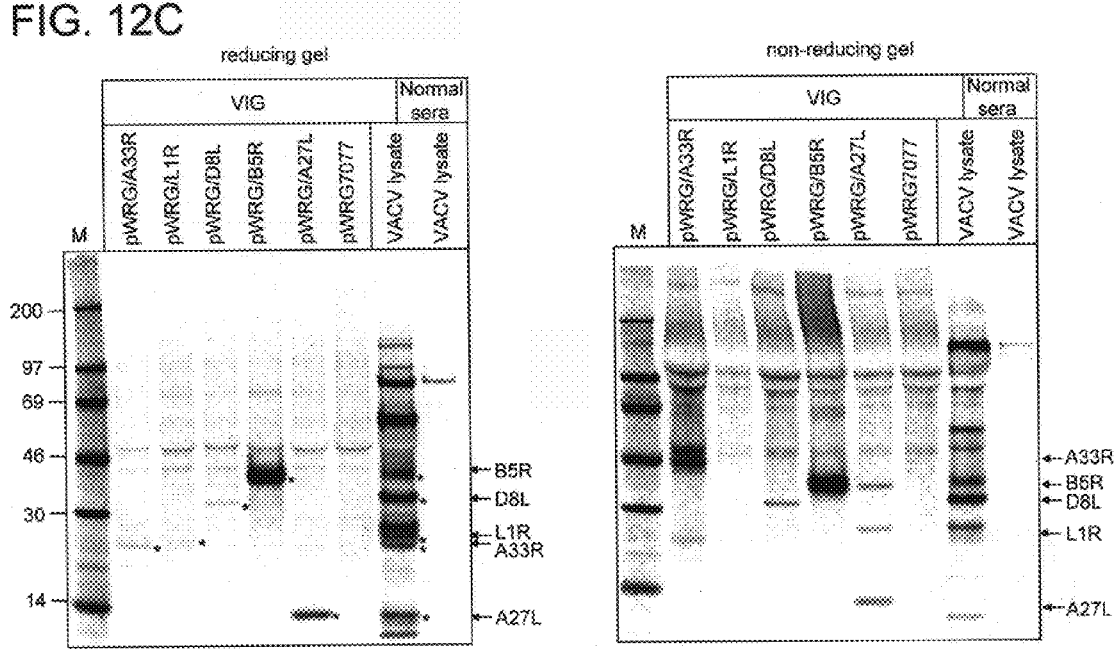

SEQUENCE LISTING

<160> NUMBER OF SEQ ID NOS: 12

<210> SEQ ID NO 1
<211> LENGTH: 753
<212> TYPE: DNA
<213> ORGANISM: Vaccinia virus, Connaught strain
<220> FEATURE:

<400> SEQUENCE: 1
atgggtgccg cagcaagcat acagacgacg gtgaatacac                40

-continued

```
tcagcgaacg tatctcgtct aaattagaac aagaagcgaa          80
cgctagtgct caaacaaaat gtgatataga aatcggaaat         120
ttttatatcc gacaaaacca tggatgtaac ctcactgtta         160
aaaatatgtg ctctgcggac gcggatgctc agttggatgc         200
tgtgttatca gccgctacag aaacatatag tggattaaca         240
ccggaacaaa aagcatacgt accagctatg tttactgctg         280
cgttaaacat tcagacaagt gtaaacactg ttgttagaga         320
ttttgaaaat tatgtgaaac aaacttgtaa ttctagcgcg         360
gtcgtcgata acaaattaaa gatacaaaac gtaatcatag         400
atgaatgtta cggagcccca ggatctccaa caaatttgga         440
atttattaat acaggatcta gcaaaggaaa ttgtgccatt         480
aaggcgttga tgcaattgac tactaaggcc actactcaaa         520
tagcacctaa acaagttgct ggtacaggag ttcagtttta         560
tatgattgtt atcggtgtta taatattggc agcgttgttt         600
atgtactatg ccaagcgtat gctgttcaca tccaccaatg         640
ataaaatcaa acttatttta gccaataagg aaaacgtcca         680
ttggactact tacatggaca cattctttag aacttctccg         720
atggttattg ctaccacgga tatgcaaaac tga                753
```

<210> SEQ ID NO 2
<211> LENGTH: 558
<212> TYPE: DNA
<213> ORGANISM: Vaccinia virus, Connaught strain
<220> FEATURE:

<400> SEQUENCE: 2

```
atgatgacac cagaaaacga cgaagagcag acatctgtgt          40
tctccgctac tgtttacgga gacaaaattc agggaaagaa          80
taaacgcaaa cgcgtgattg gtctatgtat tagaatatct         120
atggttattt cactactatc tatgattacc atgtccgcgt         160
ttctcatagt gcgcctaaat caatgcatgt ctgctaacga         200
ggctgctatt actgacgccg ctgttgccgt tgctgctgca         240
tcatctactc atagaaaggt tgcgtctagc actacacaat         280
atgatcacaa agaaagctgt aatggtttat attaccaggg         320
ttcttgttat atattacatt cagactacca gttattctcg         360
gatgctaaag caaattgcac tgcggaatca tcaacactac         400
ccaataaatc cgatgtcttg attacctggc tcattgatta         440
tgttgaggat acatggggat ctgatggtaa tccaattaca         480
aaaactacat ccgattatca agattctgat gtatcacaag         520
aagttagaaa gtatttttgt gttaaaacaa tgaactaa           558
```

<210> SEQ ID NO 3
<211> LENGTH: 34
<212> TYPE: DNA
<213> ORGANISM: artificial sequence

```
<220> FEATURE:
<223> OTHER INFORMATION: /note="PCR primer sequence derived from genomic
      sequence"

<400> SEQUENCE: 3
gccgcggccg catggtgccg cagcaagcat acag                              34

<210> SEQ ID NO 4
<211> LENGTH: 35
<212> TYPE: DNA
<213> ORGANISM: artificial sequence
<220> FEATURE:
<223> OTHER INFORMATION: /note="PCR primer sequence derived from genomic
      sequence"

<400> SEQUENCE: 4
gccggcggcc gctcagtttt gcatatccgt ggtag                             35

<210> SEQ ID NO 5
<211> LENGTH: 34
<212> TYPE: DNA
<213> ORGANISM: artificial sequence
<220> FEATURE:
<223> OTHER INFORMATION: /note="PCR primer sequence derived from genomic
      sequence"

<400> SEQUENCE: 5
gccggcggcc gcatgatgac accagaaaac gacg                              34

<210> SEQ ID NO 6
<211> LENGTH: 33
<212> TYPE: DNA
<213> ORGANISM: artificial sequence
<220> FEATURE:
<223> OTHER INFORMATION: /note="PCR primer sequence derived from genomic
      sequence"

<400> SEQUENCE: 6
gccggcggcc gcttagttca ttgttttaac aca                               33

<210> SEQ ID NO 7
<211> LENGTH: 333
<212> TYPE: DNA
<213> ORGANISM: Vaccinia virus, Connaught strain
<220> FEATURE:

<400> SEQUENCE: 7
atggacggaa ctcttttccc cggagatgac gatcttgcaa                        40
ttccagcaac tgaattttt tctacaaagg ctgctaaaaa                         80
gccagaggct aaacgcgaag caattgttaa agccgatgaa                        120
gacgacaatg aggaaactct caaacaacgg ctaactaatt                        160
tggaaaaaaa gattactaat gtaacaacaa agtttgaaca                        200
aatagaaaag tgttgtaaac gcaacgatga agttctattt                        240
aggttggaaa atcacgctga aactctaaga gcggctatga                        280
tatctctggc taaaaagatt gatgttcaga ctggacggcg                        320
tccatatgag taa                                                     333

<210> SEQ ID NO 8
<211> LENGTH: 954
<212> TYPE: DNA
<213> ORGANISM: Vaccinia virus, Connaught strain
```

```
<220> FEATURE:

<400> SEQUENCE: 8
atgaaaacga tttccgttgt tacgttgtta tgcgtactac           40
ctgctgttgt ttattcaaca tgtactgtac ccactatgaa           80
taacgctaaa ttaacgtcta ccgaaacatc gtttaatgat          120
aaacagaaag ttacatttac atgtgatcag ggatatcatt          160
ctttggatcc aaatgctgtc tgcgaaacag ataaatggaa          200
atacgaaaat ccatgcaaga aaatgtgcac agtttctgat          240
tatgtctctg aattatatga taagccatta tacgaagtga          280
attccaccat gacactaagt tgcaacggcg aaacaaaata          320
ttttcgttgc gaagaaaaaa atggaaatac ttcttggaat          360
gatactgtta cgtgtcctaa tgcggaatgt caacctcttc          400
aattagaaca cggatcgtgt caaccagtta agaaaaata           440 ctcatttggg gaatatataa ctatcaactg tgatgttgga          480
tatgaggtta ttggtgcttc gtacataagt tgtacagcta          520
attcttggaa tgttattcca tcatgtcaac aaaaatgtga          560
tatgccgtct ctatctaacg gattaatttc cggatctaca          600
ttttctatcg gtggcgttat acatcttagt tgtaaaagtg          640
gttttatact aacgggatct ccatcatcca catgtatcga          680
cggtaaatgg aatcccatac tcccaacatg tgtacgatct          720
aacaaagaat ttgatccagt ggatgatggt cccgacgatg          760
agacagattt gagcaaactc tcgaaagacg ttgtacaata          800
tgaacaagaa atagaatcgt tagaagcaac ttatcatata          840
atcatagtgg cgttaacaat tatgggcgtc atatttttaa          880
tctccgttat agtattagtt tgttcctgtg acaaaaataa          920
tgaccaatat aagttccata aattgctacc gtaa                954
```

```
<210> SEQ ID NO 9
<211> LENGTH: 42
<212> TYPE: DNA
<213> ORGANISM: Artificial sequence
<220> FEATURE:
<223> OTHER INFORMATION: /note="PCR primer sequence derived from genomic
      sequence"

<400> SEQUENCE: 9
gccggcggcc gcgccaccat ggacggaact cttttccccg ga         42
```

```
<210> SEQ ID NO 10
<211> LENGTH: 33
<212> TYPE: DNA
<213> ORGANISM: Artificial sequence
<220> FEATURE:
<223> OTHER INFORMATION: /note="PCR primer sequence derived from genomic
      sequence"

<400> SEQUENCE: 10
gcgcagatct ttactcatat ggacgccgtc cag                   33
```

-continued

```
<210> SEQ ID NO 11
<211> LENGTH: 42
<212> TYPE: DNA
<213> ORGANISM: Artificial sequence
<220> FEATURE:
<223> OTHER INFORMATION: /note="PCR primer sequence derived from genomic
      sequence"

<400> SEQUENCE: 11
gccggcggcc gcgccaccat gaaaacgatt tccgttgtta cg                              42

<210> SEQ ID NO 12
<211> LENGTH: 33
<212> TYPE: DNA
<213> ORGANISM: Artificial sequence
<220> FEATURE:
<223> OTHER INFORMATION: /note="PCR primer sequence derived from genomic
      sequence"

<400> SEQUENCE: 12
gcgcagatct ttacggtagc aatttatgga act                                       33
```

DNA VACCINES AGAINST POXVIRUSES

This application claims the benefit of priority from Provisional application Ser. No. 60/187,608 filed on Mar. 7, 2000.

Viruses in the family Poxviridae, including vaccinia virus (VACV) and variola virus, are characterized by a large linear double-stranded DNA genome (130–300 kb) packaged in a relatively large virion (~350×270 nm), and a cytoplasmic site of replication (reviewed by Moss, 1996, In "Fields Virology", D. M. Knipe et al. Eds., vol. 3, pp 2637–2671. Lippincott-Raven, Philadelphia). Assembly of VACV virions begins with condensation of dense granular material into membrane-wrapped particles called intracellular mature virions (IMV). Recent findings indiate the IMV are wrapped by a single membrane (Hollingshead et al., 1999, J. Virol. 73, 1503–1517) rather than a double membrane as previously reported. IMV are then enveloped in two additional membranes derived from the trans Golgi to form multiple membrane-warpped particles called intracellular enveloped virions (IEV) (Schmelz et al., 1994, J. Virol. 68, 130–147). IEV are moved, possibly by actin polymerization (Cudmore et al., 1995, Nature 378, 636–638), to the cell periphery, where the outermost membrane fuses with the cell plasma membrane, exposing a cell-associated eneveloped virion (CEV) (Blasco and Moss, 1991, J. Virol. 65, 5910–5920). CEV are released from the cell as extracellular enveloped virions (EEV), which play a role in long-range spread of the virus (Payne, 1980, J. Gen. Virol. 50, 89–100). IMV released from disrupted cells and EEV are both infectious forms of VACV.

The current smallpox vaccine (live vaccinia virus) has many drawbacks including: adverse reactions, scarring, ocular autoinoculation, dissemination in immunocompromised persons, and dwindling stocks. Cell culture derived vaccines, are being developed; however, these vaccines are also live viruses and pose many of the same drawbacks that plague the current vaccine. A DNA-based replacement vaccine could conceivably effectively protect against smallpox, other poxviruses, and engineered vaccinia viruses without any of the drawbacks associated with live-virus vaccines. This is especially relevant to immunocompromised persons who cannot be vaccinated with live vaccinia virus.

Naked DNA vaccines have been used to generate protective immune responses against numerous pathogenic agents, including many viruses (Gregoriadis, 1998, Pharmacol. Res. 15, 661–670). In general, naked DNA vaccines involve vaccination with plasmid DNA that contains a gene of interest controlled by a cytomegalovirus (CMV) promoter. When the plasmid is introduced into mammalian cells, cell machinery transcribes and translates the gene. The expressed protein (immunogen) is then presented to the immune system where it can elicit an immune response. One method of introducing DNA into cells is by using a gene gun. This method of vaccination involves using pressurized helium gas to accelerate DNA-coated gold beads into the skin of the vaccinee.

To identify potential targets for poxvirus vaccines or therapeutics, we generated and characterized a panel of VACV-specific monoclonal antibodies (MAbs). Passive protection experiments in mice indicated that neutralizing MAbs binding a 29-kDa protein (e.g., MAb-10F5, MAb-7D11), and nonneutralizing MAbs binding a 23- to 28-kDa protein (e.g., MAb-1G10) protected against challenge with VACV (strain WR). The target of MAb-7D11 was the product of the L1R gene (Wolffe et al. 1995, Virology 211, 53–63), and the target of MAb-1G10 was the product of the A33R gene (Roper et al., 1996, J. Virol. 70, 3753–3762). In this report, the L1R and A33R gene products will be called L1R and A33R, respectively. L1R is an essential myristoylated protein associated with the IMV membrane and is thought to play a role in IMV attachment or penetration (Franke et al., 1990, J. Virol. 64, 5988–5996; Ravanello et al., 1993, J. Gen. Virol. 75, 1479–1483; Ichihashi et al., 1994, Virology 202, 834–843; Ravanello and Hruby, 1994, J. Gen. Virol. 75, 1479–1483; Wolffe et al., 1995, supra). A33R is a nominally nonessential glycosylated/palmitated protein that forms dimers and is incorporated into the outer membrane of EEV (Payne, 1992, Virology 187, 251–260; Roper et al., 1996, supra). A33R is thought to be involved in facilitating direct cell-to-cell spread via actin-containing microvilli (Roper et al., 1998, J. Virol. 72, 4192–4204). Homologs of L1R and A33R are present in other Orthopoxviruses, e.g. between VACV and variola, L1R identity is 99.6% and A33R is 94.1% (Massung et al., 1994, Virology 201, 215–240).

To determine whether vaccination with the L1R, encoding an IMV immunogen and/or A33R, encoding an EEV immunogengene could elicit protective immunity, we constructed plasmids expressing either L1R or A33R under control of the CMV promoter and tested these plasmids, and combinations of these plasmids, for immunogenicity and protective efficacy in mice. Our results indicated that vaccination with both L1R and A33R proteins, when loaded on different gold beads and hence delivered to different cells, was more effective than vaccination with either protein by itself or vaccination with L1R and A33R on the same particle.

Furthermore, our data indicates that a composition consisting of a combination of vaccinia IMV and EEV immunogens would provide a better vaccine protective against two infectious forms of vaccinia. Thus, this invention could serve to replace the existing vaccine, and could serve to vaccinate the subpopulation that cannot be vaccinated with a live virus vaccine.

SUMMARY OF THE INVENTION

In this report, we describe a new recombinant DNA vaccine approach that involves vaccination with naked DNA expressing individual poxvirus cDNAs. Naked DNA vaccination involves delivery of plasmid DNA constructs with a gene(s) of interest into the tissue of the vaccinee (reviewed in Robinson and Torres, 1997, Semin. Immunol. 9, 271–283; and Gregoriadis, 1998, Pharm. Res. 15, 661–670). The gene(s) of interest is controlled by a mammalian or virus promoter (e.g., the cytomegalovirus immediate early promoter) that facilitates expression of the naked DNA gene product(s) within the vaccinee's cells. This intracellular expression can elicit both humoral and cell-mediated immune responses (Robinson and Torres, 1997, supra; and Gregoriadis, 1998, supra). Methods of DNA delivery include needle inoculation, oral or pulmonary delivery, and inoculation by particle bombardment (i.e., gene gun). DNA vaccination by each of these methods elicits protective immunity against many different pathogens including numerous viruses (Robinson and Torres, 1997,supra; and Gregoriadis, 1998, supra).

In this report, we demonstrate that naked DNA vaccination with a combination of IMV and EEV immunogens, for example, L1R and/or A33R, respectively, elicits poxvirus-specific antibody responses in rodents. More importantly, we demonstrate that DNA vaccination with the L1R and A33R elicits neutralizing antibodies and protects mice against a lethal poxvirus infection.

Therefore, it is one object of the present invention to provide a poxvirus DNA vaccine comprising a poxvirus cDNA. More specifically, the present invention relates to a poxvirus DNA vaccine comprising genes found in the intracellular mature form of the virus (IMV) for example, L1R and A27L in combination with genes found in the extracellular enveloped form of the virus (EEV) for example, A33R and B5R. The vaccine may consist of preferably one gene from IMV and one from EEV, more preferably, the vaccine may consist of three or four genes where at least one gene is from EEV and one is from IMV.

It is another object of the present invention to provide a method for eliciting in a subject an immune response against poxvirus, the method comprising administering to a subject a DNA fragment comprising a poxvirus cDNA. More specifically, the present invention relates to a method for eliciting an immune response against poxvirus by providing an IMV gene and an EEV gene.

In one aspect of the invention, the DNA vaccine is delivered by coating a small carrier particle with the DNA vaccine and delivering the DNA-coated particle into an animal's epidermal tissue via particle bombardment. This method may be adapted for delivery to either epidermal or mucosal tissue, or delivery into peripheral blood cells, and thus may be used to induce humoral, cell-mediated, and secretory immune reponses in the vaccinated individual. In one aspect of the invention, the IMV and EEV cDNA is delivered by coating different carrier particles and not combined on one carrier particle.

The DNA vaccine according to the present invention is inherently safe, is not painful to administer, and should not result in adverse side effects to the vaccinated individual. In addition, the invention does not require growth or use of poxvirus, which may be spread by aerosol transmission.

BRIEF DESCRIPTION OF THE DRAWINGS

These and other features, aspects, and advantages of the present invention will become better understood with reference to the following description, appended claims, and accompanying drawings where:

FIG. 2. VACV-neutralizing antibody response elicited by gene gun vaccination with pWRG/L1R. Mean PRNT values of 10 mice vaccinated with pWRG/L1R, or 10 mice scarified with VACV are shown. Also shown are the mean PRNT values of groups of 10 mice vaccinated with pWRG/A33R, pWRG/A33R plus pWRG/L1R combined on the same gold beads, or a negative control plasmid. Titrations of postitive control antibody ascitic fluid, MAb-7D11 and VACV HMAF, are also shown.

FIG. 3. Anti-A33R antibody response elicited by gene gun vaccination with pWRG/A33R. To measure the anti-A33R response, COS cell monolayers transfected with pWRG/A33R were fixed and then incubated with serial twofold dilutions of serum or control antibodies. Mean O.D. values of 10 mice vaccinated with the indicated immunogen and titrations of postitive control antibody ascitic fluid, MAb-1G10 and VACV HMAF, are shown.

FIGS. 5A and 5B. Protection experiment. Vaccinated animals (see Experiment 2, Table 1 and FIG. 4) were challenged i.p. with $5\times10^8$ PFU of VACV WR (12.5 $LD_{50}$). A. The number of survivors each day after challenge are shown. B. Mice were weighed at the indicated day postchallenge and the percentage of starting weight was calculated. Mean weight values for mice in groups 2, 3, 7, and 10, that ultimately survived the challenge, are shown. For each group, animals with the highest and lowest weight change were excluded from the calculations.

FIG. 9. Prechallenge antibody titers and survival data. Sera from mice vaccinated as described were evaluated for anti-A27L activity by PRNT, for anti-A33R activity by ELISA and for anti-B5R by ELISA. Sera were collected immediately before challenge. PRNT and ELISA titers for individual mice in each group are shown. Filled bars represent animals that did not survive challenge, and cross-hatched bars represent survivors. For the scarified mice, the PRNT values represent all VACV neutralizing antibodies, not just the anti-L1R response.

FIGS. 11A and 11B. (A) Monkeys vaccinated as described were evaluated for anti-A27L activity by PRNT, for anti-A33R activity by ELISA and for anti-B5R by ELISA. (B) Immune response in monkeys measured by cell lysate ELISA and by virion ELISA.

FIGS. 12A, 12B, and 12C. (A) Immunoprecipiations from sera of gene gun vaccinated monkey or live VACV vaccinated monkeys. (B) Immunoprecipitations using antibodies specific for antigens and sera from recently vaccinated humans with smallpox vaccine, and (C) immunoprecipitation in vaccinated humans using human antibody VIG.

DETAILED DESCRIPTION

Figure 1A:
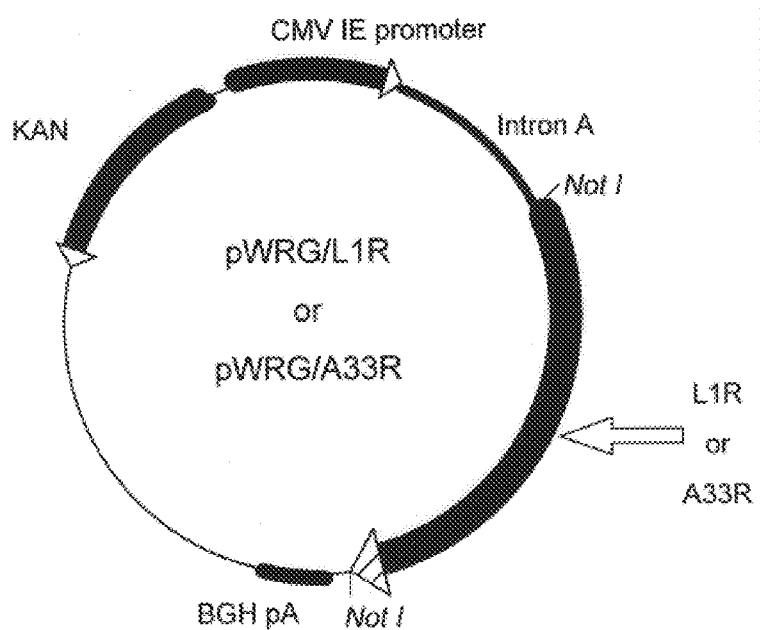
FIGS. 1A, 1B and 1C. Naked DNA constructs expressing VACV L1R or A33R genes. A. The L1R and A33R genes from VACV (Connaught strain) were PCR amplified and cloned into a naked DNA expression vector pWRG7077 to yield constructs pWRG/L1R and pWRG/A33R, respectively. The VACV genes are flanked by a cytomegalovirus immediate early promoter (CMV IE) and intron A at the 5' end of the gene and a bovine growth hormone polyadenylation signal (BGH pA) at the 3' end. Kanamycin antibiotic resistance gene (KAN). B. Expression products from COS cell monolayers transfected with pWRG/A33R, or mock transfected, were immunoprecipitated with MAb-1G10. Samples were boiled in reducing or nonreducing sample buffer, and separated by SDS-PAGE. C. Expression products from COS cell monolayers transfected with pWRG/L1R, or mock transfected, were immunoprecipitated with the L1R-specific antibody MAb-10F5. Samples were boiled in reducing or nonreducing sample buffer, and separated by SDS-PAGE. Molecular mass markers in kDa are shown at right of each gel.

In this application is described a composition and method for the vaccination of individuals against poxvirus. The method comprises delivery of a DNA encoding a poxvirus antigen to cells of an individual such that the antigen is expressed in the cell and an immune response is induced in the individual.

DNA vaccination involves administering antigen-encoding polynucleotides in vivo to induce the production of a correctly folded antigen(s) within the target cells. The introduction of the DNA vaccine will cause to be expressed within those cells the structural protein determinants associated with the pathogen protein or proteins. The processed structural proteins will be displayed on the cellular surface of the transfected cells in conjunction with the Major Histocompatibility Complex (MHC) antigens of the normal cell. Even when cell-mediated immunity is not the primary means of preventing infection, it is likely important for resolving established infections. Furthermore, the structural proteins released by the expressing transfected cells can also be picked up by antigen-presenting cells to trigger systemic humoral antibody responses.

In one embodiment, the present invention relates to a DNA or cDNA segment which encodes an IMV or an EEV antigen from a poxvirus. Genome sequences of different strains of VACV have been published and are publicly available. The VACV (Copenhagen strain) sequence (accession number M35027) can be used to deduce primer sequences for the genes of interest as described below for deducing the sequence of the VACV Connaught strain. The VACV Connaught strain L1R (SEQ ID NO:1) and A33R (SEQ ID NO:2) sequence have been deposited as Genebank #Af226617 and Genebank #Af226618, respectively. L1R and A33R homologs from other poxviruses can be used as immunogens to induce a immune response in an individual against poxviruses since the homologs in other poxviruses have high identity with the VACV proteins. Homologs include genes sharing a common evolutionaly origin, structure/function, and the products of which, encode proteins with amino acid sequence identity of at least 20%, preferably at least 30%, more preferably at least 50%, and most preferably means at least 80%. A homolog can be identified by methods known in the art such as comparison of the nucleic acid or amino acid sequences to each other using computer programs, such as BLAST, or by hybridization under stringencies which are designed to detect a predetermined amount of mismatch between the sequences. Other strains of vaccinia are expected to contain sequences at least 90% identical which will likely produce antigens capable of eliciting protective/neutralizing antibodies. Such strains include IHD, Brighton, WR, Lister, Copenhagen, Ankara. In addition, homologs of these vaccinia antigens having at least 90% identity exist in other poxviruses, such as Orthopoxvirus, such as camelpox virus, cowpox virus, ectromelia virus, monkeypox virus, raccoon poxvirus, skunk poxvirus, Tatera poxvirus, Uasin Gishu virus, variola virus, Volepox virus, Parapoxvirus such as Ausdyk virus, Bovin papular stomatitis virus, orf virus, pseudocowpox virus, red deer poxvirus, seal parapoxvirus, Capripoxvirus such as sheep-pox virus, goatpox virus lumpyskin disease virus, Suipoxvirus such as swinepox virus, Leporipoxvirus such as myxoma virus fibroma virus, hare fibroma virus, squirrel fibroma virus, western squirrel fibroma, Avipoxvirus of many species, Yatapoxvirus such as Tantpox virus, Yabapoxvirus, Molluscipoxvirus such as molluscum contagiosum virus, macropod poxvirus, crocodilian poxvirus, among others. Because of the high identity between poxviruses, it is expected that vaccines of the present invention would provide cross protection between different poxviruses.

Nucleic acids encoding IMV antigens include L1R, A27L, A3L, A10L, A12L, A13L, A14L, A17L, D8L, H3L, L4R, G7L, and 15L (Takahashi et al., 1994, Virology 202, 811–852). Nucleic acids encoding EEV antigens include A33R (Roper et al., 1996, J. Virol. 70, 3753–3762), A34R (Duncan and Smith, 1992, J. Virol. 66, 1610–1621), A36R (Parkinson and Smith, 1994, Virology 204, 376–390), A56R (Payne and Norrby, 1976, J. Gen. Virol. 32, 63–72; Shida, H., 1986, Virology 150, 451–462), B5R (Engelstad et al., 1992, Virology 188, 801–810; Isaacs et al., 1992, J. Virol. 66, 7217–7224), and F13L (Hirt et al., 1986, J. Virol. 58, 757–764). DNA or nucleic acid sequences to which the invention also relates include fragments of the IMV or EEV genes from poxviruses containing protective epitopes or antigenic determinants. Such epitopes may be conformational. The vaccine of the present invention can comprise three or more vaccinia virus nucleic acids (or nucleic acids from other poxviruses coding for homologous antigens) where at least one nucleic acid encodes an antigen found on the IMV and at least one nucleic acid encodes an antigen found on the EEV. For example, two IMV genes are L1 and A27L, and two EEV genes are A33R and B5R. The vaccine may consist of one of the following combinations: L1R+A33R; L1R+A33R+B5R; L1R+A33R+A27L; A27L+A33R+B5R; L1R+A27L+B5R; L1R+A33R+A27L, etc. or any other combination of IMV gene and EEV gene (or a homolog of the IMV and EEV genes in other poxviruses).

The sequence of nucleic acids encoding antigens found in the IMV or the EEV may be generated in any manner, including for example, chemical synthesis or DNA replication or reverse transcription or transcription, which are based on the information provided by the sequence bases in the region(s) from which the polynucleotide is derived. In addition, combinations of regions corresponding to that of the designated sequence may be modified in ways known in the art to be consistent with an intended use. The sequences of the present invention can be used in diagnostic assays such as hybridization assays and polymerase chain reaction (PCR) assays for the detection of poxvirus.

L1R and A33R sequences were derived from the VACV (Connaught strain) by PCR and cloned into pWRG7077 to yield naked DNA expression plasmids pWRG/L1R, respectively. It is understood in the art that certain changes to the nucleotide sequence employed in a genetic construct have little or no bearing on the proteins encoded by the construct, for example due to the degeneracy of the genetic code. Such changes result either from silent point mutations or point mutations that encode different amino acids that do not appreciably alter the behavior of the encoded protein. It is also understood that portions of the coding region can be eliminated without affecting the ability of the construct to achieve the desired effect, namely induction of a protective immune response against poxvirus. It is further understood in the art that certain advantageous steps can be taken to increase the antigenicity of an encoded protein by modifying its amino acid composition. Such changes in amino acid composition can be introduced by modifying the genetic sequence encoding the protein. It is contemplated that all such modifications and variations of the L1R and A33R genes of poxvirus are equivalents within the scope of the present invention.

The DNA encoding the desired antigen can be introduced into the cell in any suitable form including, a linearized plasmid, a circular plasmid, a plasmid capable of replication, an episome, RNA, etc. Preferably, the gene is contained in a plasmid. In a particularly preferred embodiment, the plasmid is an expression vector. Individual expression vectors capable of expressing the genetic material can be produced using standard recombinant techniques. Please see e.g., Maniatis et al., 1985 *Molecular Cloning: A Laboratory Manual* or *DNA Cloning*, Vol. I and II (D. N. Glover, ed., 1985) for general cloning methods.

Therefore, in another embodiment, the present invention relates to a recombinant DNA molecule that includes a vector and a DNA sequence as described above. The vector can take the form of a plasmid such as pCRII (Invitrogen) or pJW4303 (Konishi, E. et al., 1992, *Virology* 188:714), or any expression vector such as viral vectors e.g. adenovirus or Venezuelan equine encephalitis virus and others known in the art. Preferably, a promoter sequence operable in the target cell is operably linked to the DNA sequence. Several such promoters are known for mammalian systems which may be joined 5', or upstream, of the coding sequence for the encoded protein to be expressed. A suitable promoter is the human cytomegalovirus immediate early promoter. A downstream transcriptional terminator, or polyadenylation sequence, such as the polyA addition sequence of the bovine growth hormone gene, may also be added 3' to the protein coding sequence.

A suitable construct for use in the method of the present invention is pWRG7077 (4326 bp) (PowderJect Vaccines, Inc., Madison, Wis.), FIG. 1. pWRG7077 includes a human cytomegalovirus (hCMV) immediate early promoter (IE) and a bovine growth hormone polyA addition site. Between the promoter and the polyA addition site is Intron A, a sequence that naturally occurs in conjunction with the hCMV IE promoter that has been demonstrated to increase transcription when present on an expression plasmid. Downstream from Intron A, and between Intron A and the polyA addition sequence, are unique cloning sites into which the poxvirus DNA can be cloned. Also provided on pWRG7077 is a gene that confers bacterial host-cell resistance to kanamycin. Any of the fragments that encode L1R and A33R can be cloned into one of the cloning sites in pWRG7077, using methods known to the art.

In a further embodiment, the present invention relates to host cells stably transformed or transfected with the above-described recombinant DNA construct. The host cell can be prokaryotic such as Bacillus or *E. coli*, or eukaryotic such a Saccharomyces or Pichia, or vertebrate cells, mammalian cells or insect cells. The vector containing the poxvirus sequence is expressed in the bacteria and the expressed product used for diagnostic procedures or as a vaccine. Please see e.g., Maniatis et al., 1985 *Molecular Cloning: A Laboratory Manual* or *DNA Cloning*, Vol. I and II (D. N. Glover, ed., 1985) for general cloning methods. The DNA sequence can be present in the vector to a DNA encoding an agent for aid in purification of poxvirus proteins or peptides. The transformed or transfected host cells can be used as a source of DNA sequences described above. When the recombinant molecule takes the form of an expression system, the transformed or transfected cells can be used as a source of the protein or peptide encoded by the DNA. The DNA can be used as circular or linear, or linearized plasmid as long as the poxvirus sequences are operably linked to a promoter which can be expressed in the transfected cell.

In this application we describe the elicitation of protective immunity to poxviruses by DNA vaccines. The DNA can be delivered by injection into the tissue of the recipient, oral or pulmonary delivery and inoculation by particle bombardment (i.e., gene gun). Any of these methods can be used to deliver DNA as long as the DNA is expressed and the desired antigen is made in the cell. Two methods are exemplified in this application, both shown to be successful in eliciting a protective immune response in the vaccinee.

To deliver DNA vaccines by particle bombardment, we chose to use the PowderJect-XR™ gene gun device described in WO 95/19799, Jul. 27, 1995. Other instruments are available and known to people in the art. This instrument, which delivers DNA-coated gold beads directly into epidermal cells by high-velocity particle bombardment, was shown to more efficiently induce both humoral and cell-mediated immune responses, with smaller quantities of DNA, than inoculation of the same DNAs by other parenteral routes (Eisenbraun, M. et al., 1993, *DNA Cell. Biol.* 12: 791; Fynan, E. F. et al., 1993, *Proc. Natl. Acad. Sci. USA* 90: 11478; Haynes, J. R. et al., 1994, *AIDS Res. Hum. Retroviruses* 10: Suppl. 2:S43; Pertmer, T. M. et al., 1995, *Vaccine* 13: 1427). Epidermal inoculation of the DNA candidate vaccines also offers the advantages of gene expression in an immunologically active tissue that is generally exfoliated within 15 to 30 days, and which is an important natural focus of viral replication after tick-bite (Bos, J. D., 1997, *Clin. Exp. Immunol.* 107 Suppl. 1:3; Labuda, M. et al., 1996, *Virology* 219:357; Rambukkana, A. et al., 1995, *Lab. Invest.* 73:521; Stingl, G., 1993, *Recent Results Cancer Res.* 128:45).

Candidate vaccines include particles having nucleic acids encoding IMV antigens and particles having nucleic acids encoding EEV antigens. The IMV and EEV antigens can be derived from other other Orthopoxviruses including variola virus, monkeypox virus, cowpox virus, Parapoxviruses such as orf virus, paravaccinia virus, and unclassified poxviruses such as Tanapoxvirus, Yabapoxvirus and Molluscum contagiosum.

In addition, the present invention relates to a vaccine comprising one or more DNAs from different poxviruses. Such a vaccine is referred to as a multivalent vaccine. The vaccine is designed to protect against pathologies resulting from exposure to one or several poxviruses. The DNA segments from different viruses can be on different particles or on the same particle, whichever results in the desired immune response. The vaccine can also be combined with reagents which increase the antigenicity of the vaccine, or reduce its side effects.

The technique of accelerated particles gene delivery or particle bombardment is based on the coating of DNA to be delivered into cells onto extremely small carrier particles, which are designed to be small in relation to the cells sought to be transformed by the process. The DNA sequence containing the desired gene can be simply dried onto a small inert particle. The particle may be made of any inert material such as an inert metal (gold, silver, platinum, tungsten, etc.) or inert plastic (polystyrene, polypropylene, polycarbonate, etc.). Preferably, the particle is made of gold, platinum or tungsten. Most preferably, the particle is made of gold. Suitably, the particle is spherical and has a diameter of 0.5 to 5 microns, preferably 1 to 3 microns. DNA molecules in such a form may have a relatively short period of stability and may tend to degrade rather rapidly due to chemical reactions with the metallic or oxide substrate of the particle itself. Thus, if the carrier particles are first coated with an encapsulating agent, the DNA strands have greatly improved stability and do not degrade significantly even over a time period of several weeks. A suitable encapsulating agent is polylysine (molecular weight 200,000) which can be applied to the carrier particles before the DNA molecules are applied. Other encapsulating agents, polymeric or otherwise, may also be useful as similar encapsulating agents, including spermidine. The polylysine is applied to the particles by rinsing the gold particles in a solution of 0.02% polylysine and then air drying or heat drying the particles thus coated. Once the metallic particles coated with polylysine were properly dried, DNA strands are then loaded onto the particles.

The DNA is loaded onto the particles at a rate of between 0.5 and 30 micrograms of DNA per milligram of gold bead spheres. A preferable ratio of DNA to gold is 0.5–5.0 ug of DNA per milligram of gold.

A sample procedure begins with gamma irradiated (preferably about 30 kGy) tefzel tubing. The gold is weighed out into a microfuge tube, spermidine (free base) at about 0.05 M is added and mixed, and then the DNA is added. A 10% CaCl solution is incubated along with the DNA for about 10 minutes to provide a fine calcium precipitate. The precipitate carries the DNA with it onto the beads. The tubes are microfuged and the pellet resuspended and washed in 100% ethanol and the final product resupeded in 100% ethanol at 0.0025 mg/ml PVP. The gold with the DNA is then applied onto the tubing and dried.

The general approach of accelerated particle gene transfection technology is described in U.S. Pat. No. 4,945,050 to Sanford. An instrument based on an improved variant of that approach is available commercially from PowderJect Vaccines, Inc., Madison Wis., and is described in WO 95/19799. All documents cited herein supra and infra are hereby incorporated in their entirety by reference thereto. Briefly, the DNA-coated particles are deposited onto the interior surface of plastic tubing which is cut to a suitable length to form sample cartridges. A sample cartridge is placed in the path of a compressed gas (e.g., helium at a pressure sufficient to dislodge the particles from the cartridge e.g., 350–400 psi). The particles are entrained in the gas stream and are delivered with sufficient force toward the target tissue to enter the cells of the tissue. Further details are available in the published apparatus application.

The coated carrier particles are physically accelerated toward the cells to be transformed such that the carrier particles lodge in the interior of the target cells. This technique can be used either with cells in vitro or in vivo. At some frequency, the DNA which has been previously coated onto the carrier particles is expressed in the target cells. This gene expression technique has been demonstrated to work in prokaryotes and eukaryotes, from bacteria and yeasts to higher plants and animals. Thus, the accelerated particle method provides a convenient methodology for delivering genes into the cells of a wide variety of tissue types, and offers the capability of delivering those genes to cells in situ and in vivo without any adverse impact or effect on the treated individual. Therefore, the accelerated particle method is also preferred in that it allows a DNA vaccine capable of eliciting an immune response to be directed both to a particular tissue, and to a particular cell layer in a tissue, by varying the delivery site and the force with which the particles are accelerated, respectively. This technique is thus particularly suited for delivery of genes for antigenic proteins into the epidermis.

A DNA vaccine can be delivered in a non-invasive manner to a variety of susceptible tissue types in order to achieve the desired antigenic response in the individual. Most advantageously, the genetic vaccine can be introduced into the epidermis. Such delivery, it has been found, will produce a systemic humoral immune response.

To obtain additional effectiveness from this technique, it may also be desirable that the genes be delivered to a mucosal tissue surface, in order to ensure that mucosal, humoral and cellular immune responses are produced in the vaccinated individual. There are a variety of suitable delivery sites available including any number of sites on the epidermis, peripheral blood cells, i.e. lymphocytes, which could be treated in vitro and placed back into the individual, and a variety of oral, upper respiratory, and genital mucosal surfaces.

Gene gun-based DNA immunization achieves direct, intracellular delivery of DNA, elicits higher levels of protective immunity, and requires approximately three orders of magnitude less DNA than methods employing standard inoculation.

Moreover, gene gun delivery allows for precise control over the level and form of antigen production in a given epidermal site because intracellular DNA delivery can be controlled by systematically varying the number of particles delivered and the amount of DNA per particle. This precise control over the level and form of antigen production may allow for control over the nature of the resultant immune response.

The term transfected is used herein to refer to cells which have incorporated the delivered foreign DNA vaccine, whichever delivery technique is used.

It is herein disclosed that when inducing cellular, humoral, and protective immune repsonses after DNA vaccination the preferred target cells are epidermal cells, rather than cells of deeper skin layers such as the dermis. Epidermal cells are preferred recipients of DNA vaccines because they are the most accessible cells of the body and may, therefore, be immunized non-invasively. Secondly, in addition to eliciting a humoral immune response, DNA immunized epidermal cells also elicit a cytotoxic immune response that is stronger than that generated in subepidermal cells. Delivery to epidermis also has the advantages of being less invasive and delivering to cells which are ultimately sloughed by the body.

Although it can be desirable to induce an immune response by delivering genetic material to a target animal, merely demonstrating an immune response is not necessarily sufficient to confer protective advantage on the animal. What is important is to achieve a protective immune response that manifests itself in a clinical difference. That is, a method is effective only if it reduces the severity of the disease symptoms. It is preferred that the immunization method be at least 20% effective in preventing death in an immunized population after challenge with poxvirus. More preferably, the vaccination method is 50% or more effective, and most preferably 70–100% effective, in preventing death in an immunized population. The vaccination method is shown herein to be 100% effective in the mouse model for poxvirus. In contrast, unimmunized animals are uniformly killed by challenge with poxvirus. Our results indicate that vaccination with and IMV (L1R) and EEV (A33R) encoding nucleic acid on different particles provides the best protection against a lethal poxvirus infection.

Generally, the DNA vaccine administered may be in an amount of about 1–5 ug of DNA per dose and will depend on the subject to be treated, capacity of the subject's immune system to develop the desired immune response, and the degree of protection desired. Precise amounts of the vaccine to be administered may depend on the judgement of the practitioner and may be peculiar to each subject and antigen.

The vaccine for eliciting an immune response against one or more viruses, may be given in a single dose schedule, or preferably a multiple dose schedule in which a primary course of vaccination may be with 1–10 separate doses, followed by other doses given at subsequent time intervals required to maintain and or reinforce the immune response, for example, at 1–4 months for a second dose, and if needed, a subsequent dose(s) after several months. Examples of suitable immunization schedules include: (i) 0, 1 months and 6 months, (ii) 0, 7 days and 1 month, (iii) 0 and 1 month, (iv) 0 and 6 months, or other schedules sufficient to elicit the desired immune responses expected to confer protective immunity, or reduce disease symptoms, or reduce severity of disease.

In another embodiment, the present invention provides reagents useful for carrying out the present process. Such reagents comprise a DNA fragment containing at least one IMV or EEV antigen such as L1R or A33R from poxvirus, and a small, inert, dense particle. The DNA fragment, and dense particle are those described above.

Preferably, the DNA is frozen or lyophilized, and the small, inert, dense particle is in dry powder. If a coating solution is used, the dry ingredients for the coating solution may be premixed and premeasured and contained in a container such as a vial or sealed envelope.

The present invention also provides kits which are useful for carrying out the present invention. The present kits comprise a first container means containing the above-described frozen or lyophilized DNA. The kit also comprises a second container means which contains the coating solution or the premixed, premeasured dry components of the coating solution. The kit also comprises a third container means which contains the small, inert, dense particles in dry powder form or suspended in 100% ethanol. These container means can be made of glass, plastic or foil and can be a vial, bottle, pouch, tube, bag, etc. The kit may also contain written information, such as procedures for carrying out the present invention or analytical information, such as the amount of reagent (e.g. moles or mass of DNA) contained in the first container means. The written information may be on any of the first, second, and/or third container means, and/or a separate sheet included, along with the first, second, and third container means, in a fourth container means. The fourth container means may be, e.g. a box or a bag, and may contain the first, second, and third container means.

Other features of the invention will become apparent in the course of the following descriptions of exemplary embodiments which are given for illustration of the invention and are not intended to be limiting thereof.

The following materials and method were used in the examples below.

Materials and Methods

Viruses and cells. VACV Connaught vaccine strain (derived from the New York City Board of Health strain) (McClain et al. 1997, J. Infect. Dis. 175, 756–763) and strain WR (Western Reserve) (ATCC VR-119) were maintained in VERO cell (ATCC CRL-1587) monolayers grown in Eagle minimal essential medium, containing 5% heat-inactivated fetal bovine serum, 1% antibiotics (100 U/ml penicillin, 100 ug/ml streptomycin, and 50 ug/ml gentamicin), 10 mM HEPES (cEMEM)s. COS cells (ATCC CRL 1651) were used for transient expression experiments.

Antibodies. Two L1R-specific (MAb-7D11 and MAb-10F5) and two A33R-specific (MAb-1G10 and MAb-10F10) MAbs, as mouse ascitic fluids, were used. VACV (strain Connaught) hyperimmune mouse ascitic fluid (VACV HMAF) was also used.

Cloning L1R and A33R into naked-DNA expression plasmids. VACV (Connaught strain) DNA was purified by standard methods and used as template for PCR and cloning of the L1R and A33R genes. PCR primer design was based on the published VACV (Copenhagen strain) sequence (accession number M35027). The L1R primers were: 5'-gcc gcggccgcatggtgccgcagcaagcatacag (SEQ ID NO:3) and 5'-gccggcggccgctcagttttgcatatccgtggtag (SEQ ID NO:4); and the A33R primers were: 5'-gccg gcggccgcatgatgacaccagaaaacgacg (SEQ ID NO:5) and 5'-gccggcggccgcttagttcattgttttaacaca (SEQ ID NO:6). Not1 sites (underlined) were incorporated at gene termini. Start codons are shown in bold. L1R and A33R were PCR-amplified using VENT polymerase (NEB), cut with Not1, and cloned into the Not1 site of plasmid pWRG7077 (Schmaljohn et al., 1997, J. Virol. 71, 9563–9569) to yield naked DNA expression plasmids pWRG/L1R and pWRG/A33R, respectively.

Transient expression. Plasmid DNA was transfected into COS cell monolayers (60–80% confluent) using Lipofectin or Fugene6 reagent as described by the manufacturer. After 24–48 hr, monolayers were radiolabeled with Promix (200 uCi per T-25 flask, [$^{35}$S]methionine and [$^{35}$S]cysteine; Amersham) and immunoprecipitated as follows. Transfected cells were lysed on ice for 5 min with a modified RIPA buffer: 0.25 M NaCl, 1 mM EDTA, 1% Triton X-100, 0.5% sodium deoxycholate, 10 mM Tris, pH 7.4, and protease inhibitors (Complete; Boehringer Mannheim). To increase the yield of precipitable L1R, 10 mM iodoacetamide was included in the lysis buffer (Wolffe et al., 1995, Virology 211, 53–63). Lysates were combined with the indicated antibody (previously incubated with unlabeled COS cell lysate) and incubated overnight at 4° C. Lysate-antibody mixtures were combined with protein A sepharose (CL-4B; Sigma), incubated at 4° C. for 30 min, and then washed three times with lysis buffer and once with 10 MM Tris, pH 8.0. Sample buffer (125 mM Tris [pH 8.0], 1% SDS, 10% glycerol, 0.01% bromophenol blue containing 2% 2-mercaptoethanol for reducing gels or 10 mM iodoacetamide for nonreducing gels) was added and the samples were boiled for 2 min. Samples were then analyzed by sodium dodecyl sulfate (SDS)-10% polyacrylamide gel electrophoresis (PAGE) and subjected to autoradiography.

Vaccination with the gene gun. Cartridges for the gene gun were prepared as described previously (Eisenbraun et al., 1993, DNA Cell Biol. 12, 791–797; Schmaljohn et al., 1997, supra). Briefly, plasmid DNA was precipitated onto ~2 μm diameter gold beads (Degussa, South Plainfield, N.J.), 1 ug DNA per 1 mg gold, which were then coated on the inner surface of Tefzel tubing (McMaster-Carr). The tubing was cut into 0.5 inch cartridges. When completed, each cartridge contained 0.25–0.5 ug of DNA coated on 0.5 mg of gold. To vaccinate animals, abdominal fur was removed with clippers and DNA-coated gold was administered to two nonoverlapping sites on the abdominal epidermis by using the gene gun (Powderject Delivery Device, Powderject, Inc.) at 400 p.s.i. as described previously (Pertmer et al., 1995, Vaccine 13, 1427–1430).

Plaque reduction neutralization assay. VACV-infected cell lysate was diluted in cEMEM to give approximately 1,000 PFU/ml. Aliquots of this virus suspension (100 ul) were incubated with an equal volume of antibody diluted in cEMEM (serum samples were heat inactivated, 56° C. for 30 min, prior to dilution) for 1 hr at 37° C. and then 180 ul of sample was adsorbed to VERO cell monolayers in 6-well plates (or 12-well plates) for 1 hr. A 2 ml cEMEM liquid overlay was added to each well (1 ml for 12-swell plates). After 3 days at 37° C., monolayers were stained with 1% crystal violet dissolved in 70% ethanol. Plaques were counted and the percent neutralization was calculated relative to plaque numbers in the absence of antibody. Titers represent the reciprocal of the highest dilution resulting in a 50% reduction in the number of plaques.

Transfection/ELISA Method-COS cell monolayers, grown in 96-well cell culture plates, were transfected with pWRG/A33R (0.2 ug/well) using Fugene 6 or were mock transfected. After ~24 hr the monolayers were fixed with 1:1 acetone:methanol for 2 min and immunostained as previously described (Roper et al. 1996, J. Virol. 70, 3753–3762); however, the dianisidine substrate was replaced with 2,2'-azino bis(3-ethylbenzthiazoline-6-sulfonic acid (ABTS) substrate. Briefly, monolayers were fixed with 1:1 acetone:methanol for 2 min, rinsed with PBS, incubated 1 hr with primary antibody diluted in PBS+3% FBS, rinsed with PBS, incubated 30 min with peroxidase labeled goat anti-mouse antibody (Sigma) diluted in PBS+3% FBS, rinsed, and finally, incubated with ABTS. After ~30 min, 100 ul per well of 0.2 N phosphoric acid was added and the O.D. at 405 nm was determined by an ELISA plate reader. O.D. values from mock transfected wells were subtracted from those of transfected wells to determine the specific O.D. 405 nm for each sample. End-point titers were determined as the highest dilution with an absorbance value greater than the mean absorbance value from negative control plasmid (pWRG7077)-vaccinated animals plus three standard deviations.

Challenge experiment. Mice were injected with $5\times10^8$ PFU of VACV strain WR (12.5 $LD_{50}$) (clarified infected cell lysate) by the intraperitoneal route (i.p.) with a 0.5 mm×16 mm needle. This research was conducted in accordance with procedures described in the Guide for the Care and Use of Laboratory Animals (National Institute of Health, 1996). The facilities are fully accredited by the American Association for Accreditation of Laboratory Animal Care.

EXAMPLE 1

Cloning the vaccinia A33R and L1R genes into a naked-DNA vector and transient expression in cell culture. The A33R and L1R genes from VACV (Connaught vaccine strain) were PCR amplified and cloned into a naked-DNA expression vector pWRG7077 (Schmaljohn et al., 1997, supra) to yield constructs pWRG/A33R and pWRG/L1R, respectively (FIG. 1). Sequence analysis of the L1R (SEQ ID NO:1) and A33R (SEQ ID NO:2) clones indicated that the Connaught strain and WR strain genes are identical at the amino acid level.

Figure 1B:
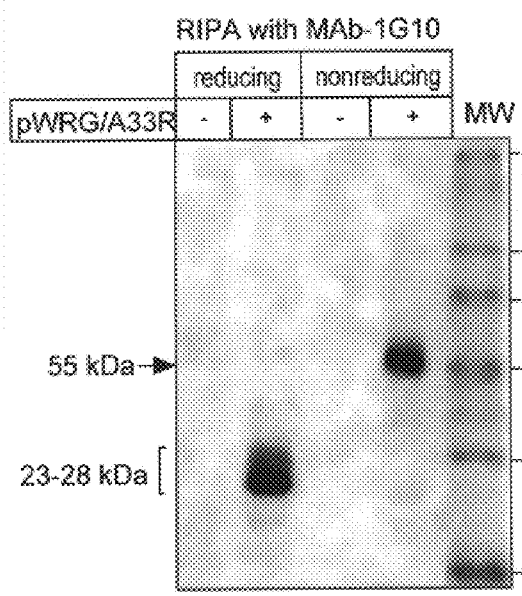
Figure 1C:
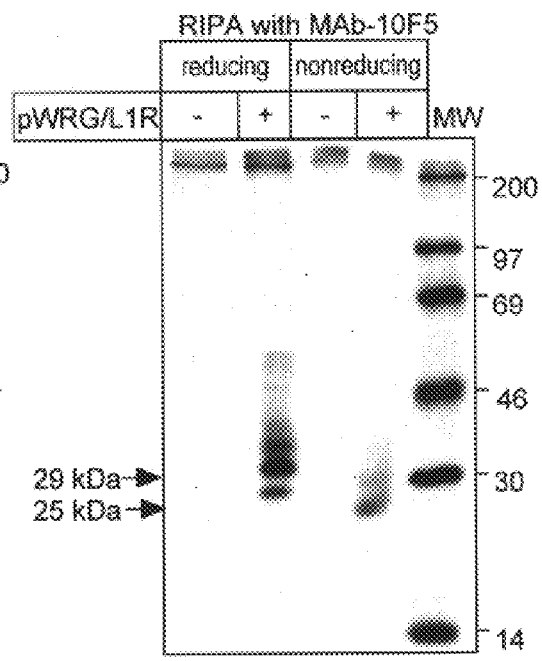

To determine if the appropriate gene products were expressed, pWRG/L1R or pWRG/A33R were transfected into COS cells and radiolabeled proteins were immunoprecipitated with MAbs specific to each protein. MAb-1G10 (A33R-specific) immunoprecipitated a product with an apparent size of 23–28 kDa under reducing conditions, and 55 kDa under nonreducing conditions (FIG. 1B). MAb-10F5 (L1R-specific) immunoprecipitated products with apparent sizes of 25 kDa and 29 kDa under reducing and nonreducing conditions (FIG. 1C). Under reducing conditions the predominant product ran at an apparent size of 29 kDa, and under nonreducing conditions the predominant product ran at an apparent size of 25 kDa. Thus, both pWRG/A33R and pWRG/L1R expressed proteins that were bound by A33R- and L1R-specific MAbs, and had predicted electrophoretic mobilities.

EXAMPLE 2

Vaccination with pWRG/L1R elicits a neutralizing antibody response in mice. To determine if vaccination with pWRG/L1R or pWRG/A33R elicited antibody responses in mice, groups of 9–10 mice were vaccinated with pWRG/L1R, pWRG/A33R, or a combination of pWRG/L1R and pWRG/A33R on the same gold beads (pWRG/L1R+pWRG/A33R[same gold]), or a negative control plasmid (pWRG7077) (Experiment 1, Table 1). As positive controls, 10 mice were vaccinated by tail scarification with VACV (Connaught strain). Sera were collected before initial vaccinations (prebleed) and 12 weeks after the final boost.

To measure L1R-specific antibody responses, we performed plaque-reduction neutralization tests (PRNT). All 10 mice vaccinated with pWRG/L1R produced VACV-specific neutralizing antibodies exhibiting PRNT titers ranging from 80 to 320, geometric mean titer (GMT)=197. Likewise, all 10 mice scarified with VACV produced neutralizing antibodies with titers ranging from 80 to 1,280, GMT=368. VACV neutralizing antibodies were not detected in prebleeds, or in sera from mice vaccinated with either pWRG/A33R or pWRG7077. Interestingly, neutralizing antibodies were not detected in any of nine mice vaccinated with pWRG/L1R+pWRG/A33R[same gold]. Mean PRNT values for vaccinated mice sera, and control antibodies are shown (FIG. 2).

TABLE 1

Vaccination Schedules of Gene Gun Experiments

| Experiment Group | Immunogen | DNA per cartridge (ug) | Number of cartridges per dose | Boost 1 (wks after priming) | Boost 2 (wks after boost2) | Final Bleed (wks after final boost) |
|---|---|---|---|---|---|---|
| 1 | (−) control[a] | 0.5 | 2 | 4 | 4 | 12 |
|   | pWRG/L1R | 0.5 | 2 | 4 | 4 | 12 |
|   | pWRG/A33R | 0.5 | 2 | 4 | 4 | 12 |
|   | pWRG/L1R + pWRGA33R [same gold] | 0.5 each | 2 | 4 | 4 | 12 |
|   | scarification | NA | NA | NA | NA | NA |

TABLE 1-continued

Vaccination Schedules of Gene Gun Experiments

| Experiment | Group | Immunogen | DNA per cartridge (ug) | Number of cartridges per dose | Boost 1 (wks after priming) | Boost 2 (wks after boost2) | Final Bleed (wks after final boost) |
|---|---|---|---|---|---|---|---|
| 2 | 1 | (−) control | 0.5 | 2 | 3 | 2 | 2 |
|   | 2 | pWRG/L1R | 0.5 | 2 | 3 | 2 | 2 |
|   | 3 | pWRG/A33R | 0.5 | 2 | 3 | 2 | 2 |
|   | 4 | pWRG/L1R + pWRGA33R [same gold] | 0.5 each | 2 | 3 | 2 | 2 |
|   | 5 | pWRG/L1R + (−) control [same gold] | 0.5 each | 2 | 3 | 2 | 2 |
|   | 6 | pWRG/A33R + (−) control [same gold] | 0.5 each | 2 | 3 | 2 | 2 |
|   | 7 | pWRG/ L1R + pWRGA33R [different gold] | 0.5 each | 1 each | 3 | 2 | 2 |
|   | 8 | pWRG/L1R + (−) control [different gold] | 0.5 | 1 each | 3 | 2 | 2 |
|   | 9 | pWRG/A33R + (−) control [different gold] | 0.5 | 1 each | 3 | 2 | 2 |
|   | 10 | Scarification[b] | NA | NA | NA | NA | 2 |

Note.
NA, not applicable
[a](−) control, negative control plasmid
[b]VACV (Connaught strain) 10 μl drop of PBS containing 8 × 106 PFU scratched into tail ~1 cm from base) as positive controls.

Thus, a neutralizing antibody response was elicited when mice were vaccinated with pWRG/L1R, but not when pWRG/L1R was combined on the same gold beads as pWRG/A33R.

EXAMPLE 3

Vaccination with pWRG/A33R elicits an antibody response in mice. To measure A33R-specific antibody responses, we developed an ELISA that uses a fixed cell monolayer, previously transfected with pWRG/A33R, as the solid-phase antigen. This ELISA is based on the observation that cells transfected with the A33R gene, or infected with VACV, exhibit a strong signal when immunostained with A33R specific MAbs (Roper et al. 1996, J. Virol. 70, 3753–3762). All 10 mice vaccinated with pWRG/A33R exhibited an anti-A33R antibody response with titers ranging from 400 to 6400, GMT=1600. Similarly, nine of nine mice vaccinated with pWRG/A33R+pWRG/L1R[same gold] exhibited an anti A33R antibody response with titers ranging from 800 to 3200, GMT=2352. Only four of 10 scarified mice exhibited detectable anti-A33R antibody responses with titers ranging from <200 to 800, GMT=174. Mean ELISA values for vaccinated mice and control antibodies are shown (FIG. 3). Positive control antibodies, MAb 1G10 and VACV HMAF, had titers of 6400 and 1600, respectively. A second anti-A33R antibody, MAb-10F10, had a titer of 3200. Thus, vaccination with pWRG/A33R alone or in combination with pWRG/L1R elicited a non-neutralizing antibody response in mice that was significantly greater than the anti-A33R response elicited by tail scarification with live VACV. This result was reproduced in three separate experiments (data not shown). Moreover, although an anti-L1R response was undetected in mice vaccinated with pWRG/L1R+pWRG/A33R [same gold] (FIG. 2), a robust anti-A33R was detected (FIG. 3).

EXAMPLE 4

Protection against lethal infection after vaccination with pWRG/L1R and/or pWRG/A33R. To test whether pWRG/L1R and/or pWRG/A33R could protect mice from lethal challenge with VACV, mice were vaccinated with a single construct or both constructs and then challenged with a lethal dose of VACV. Dual construct vaccinations were performed with either a combination of both plasmids on the same gold beads, or gold beads coated with individual constructs. The vaccination schedule of Experiment 2 is shown in Table 1.

Figure 4:
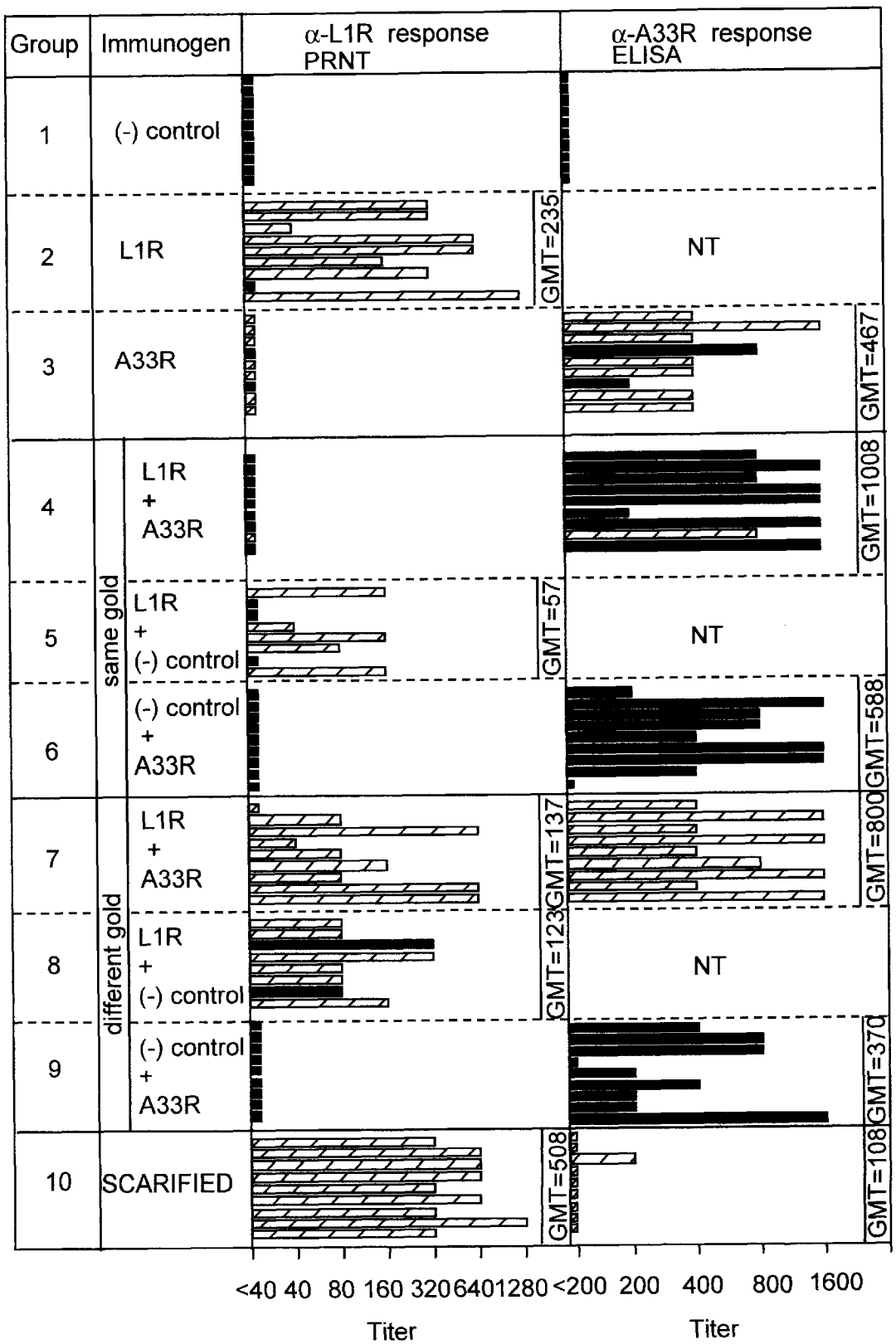
FIG. 4. Prechallenge antibody titers and survival data. Sera from mice vaccinated as described in Table 1, Experiment 2, were evaluated for anti-L1R activity by PRNT, and for anti-A33R activity by ELISA. Sera were collected immediately before challenge. PRNT and ELISA titers for individual mice in each group are shown. Filled bars represent animals that did not survive challenge, and cross-hatched bars represent survivors. For the scarified mice (Group 10), the PRNT values represent all VACV neutralizing antibodies, not just the anti-L1R response. In groups where positive antibody responses were detected, geometric mean titers (GMT) are shown. NT=not tested.

Most mice vaccinated with pWRG/L1R developed neutralizing antibodies (Groups 2,5,7,8; FIG. 4); however, as in Experiment 1, if pWRG/A33R was combined on the same gold beads with pWRG/L1R, none of the mice developed neutralizing antibodies (Group 4, FIG. 4). Most mice vaccinated with pWRG/A33R developed anti-A33R antibodies regardless of whether pWRG/L1R was present on the same gold beads (Groups 3,4,6,7,9; FIG. 4). All of the scarified mice developed neutralizing antibodies, which represent not only anti L1R antibodies, but also antibodies to other neutralizing antigens. Only one scarified mouse in Experiment 2 had an anti A33R titer 3200 (Group 10, FIG. 4).

Two weeks after the final vaccination, mice were challenged intraperitoneally (i.p.) with $5 \times 10^8$ PFU (12.5 $LD_{50}$) of VACV WR. The results of the protection experiment are shown in FIGS. 4, 5. All mice vaccinated by tail scarification survived challenge with minimal clinical signs of disease except a transient weight loss (FIG. 5). All mice vaccinated with the negative control plasmid died within 3 days (FIG. 5A). Most mice vaccinated with pWRG/L1R alone (Group 2), or combined with a negative control plasmid, on the same or different gold (Groups 5 and 8), survived challenge, suggesting vaccination with pWRG/L1R provided partial protection against an i.p. challenge with VACV WR. In most cases, the L1R vaccinated mice that succumbed did so at later times after challenge than controls (FIG. 5A). Although seven of nine mice vaccinated with pWRG/A33R alone survived challenge (Group 3), none of the mice vaccinated with pWRG/A33R combined with a negative control plasmid, on the same or different gold, survived challenge (Groups 6 and 9). Mice vaccinated with pWRG/A33R alone, that survived challenge, exhibited sustained morbidity (a greater than 10% reduction in body weight on days 2–5 post challenge) (FIG. 5B). In a follow up experiment performed to further examine the protective efficacy of vaccination with pWRG/A33R alone, 10 of 10 mice died within 4 days despite having anti-A33R antibody titers comparable to those in Group 3, FIG. 4 (data not shown). Together these data suggest that vaccination with A33R provided minimal protection against i.p. challenge with VACV WR and was not an effective vaccine against i.p. challenge.

When mice were vaccinated with both plasmids, the results differed dramatically depending on whether the plasmids were loaded on the same or different gold beads. When pWRG/A33R and pWRG/L1R were combined on the same gold beads, all but one of the mice died (Group 4). In contrast, when the plasmids were loaded on different gold beads all of the mice were protected (Group 7). Morbidity, as measured by weight loss, was similar in the scarified mice and the mice vaccinated with pWRG/L1R+pWRG/A33R [different gold] (FIG. 5B).

EXAMPLE 5

Figures 6, 7:
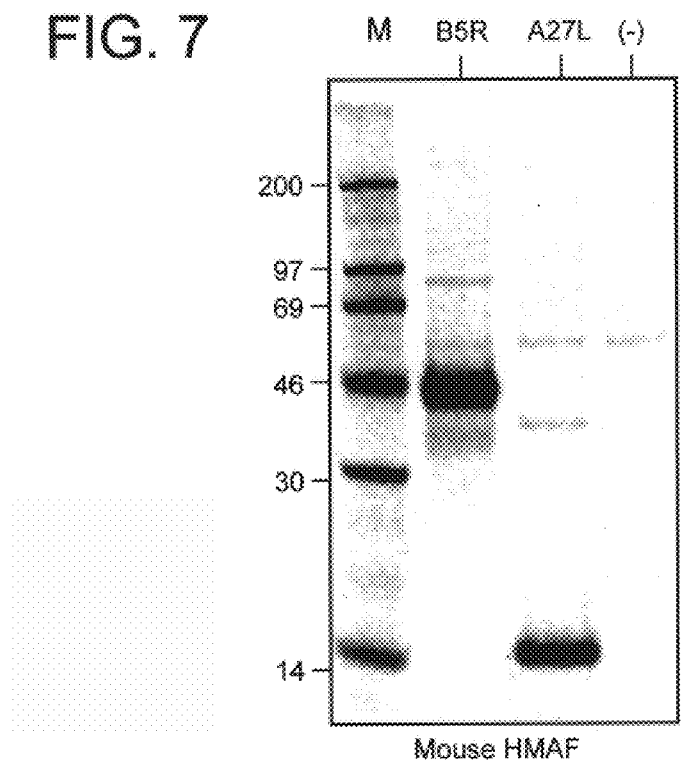
FIG. 6. Comparison between VACV and Variola virus amino acid sequences for A27L, A33R, L1R, and B5R.
FIG. 7. Expression products from COS cell monolayers transfected with pWRG/B5R, pWRG/A27L or mock transfected (−). The correct sized proteins were immunoprecipitated by mouse hyperimmune ascitic fluid against vaccinia virus. Samples were boiled in reducing or nonreducing sample buffer, and separated by SDS-PAGE. Molecular mass markers in kDa are shown at right of each gel.

Other IMV (A27L) and EEV (B5R) genes. A27L and B5R from the Connaught strain of vaccinia were PCR cloned into pWRG7077 and sequenced (A27L, SEQ ID NO: 7, B5R, SEQ ID NO: 8). The primers used to clone A27L were: 5'-GCC GGC GGC CGC GCC ACC ATG GAC GGA ACT CTT TTC CCC GGA3' (SEQ ID NO:9) and 5'-GCG CAG ATC TTT ACT CAT ATG GAC GCC GTC CAG (SEQ ID NO:10). The primers for cloning B5R were 5'-GCC GGC GGC CGC GCC ACC ATG AAA ACG ATT TCC GTT GTT ACG-3' (SEQ ID NO: 11) and 5'-GCG CAG ATC TTT ACG GTA GCA ATT TAT GGA ACT-3' (SEQ ID NO:12). These genes were found to be greater than 94% identical to their variola homologs (FIG. 6). The plasmids pWRG/A27L and pWRG/B5R were tested for expression in cell culture as described above. The VACV genes were properly expressed in COS cells transfected with the specified genes and the correct size proteins were immunoprecipitated by mouse hyperimmune ascitic fluid against vaccinia virus (FIG. 7).

Figure 8:
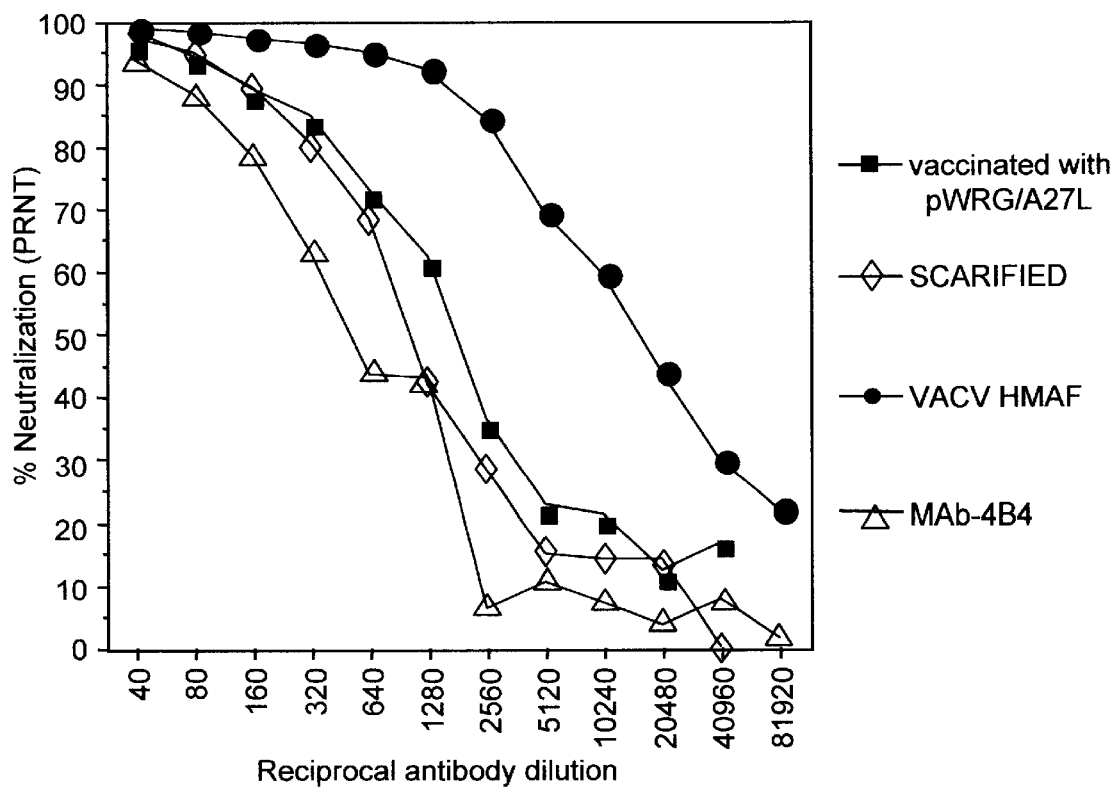
FIG. 8. Anti A27L antibody response by gene gun vaccination with pWRG/A27L.-specific monoclonal antibody ascitic fluid. To measure the anti-A27L response, COS cell monolayers transfected with pWRG/A27L were fixed and then incubated with serial twofold dilutions of serum or control antibodies. Mean O.D. values of 10 mice vaccinated with the indicated immunogen and titrations of postitive control antibody ascitic fluid, MAb-4B4 and VACV HMAF, are shown.

Mice were vaccinated with the different constructs as described in Table 2. Primary vaccination followed by first boost at 3 weeks and second boost two weeks later. Mice were challenged 2 weeks after final boost. Scarification of positive controls was performed the same way as for L1R and A33R described above. As with A33R, mice vaccinated with pWRG/A27L developed neutralizing antibody levels similar to those in scarified mice. In a PRNT assay, a A27L-specific monoclonal antibody ascitic fluid neutralized slightly less efficiently than the gene gun vaccinated mice as shown in FIG. 8.

To test whether IMV or EEV genes alone or in combination could protect mice from lethal challenge with VACV, groups of mice were vaccinated with B5R alone, A27L alone, a combination of both genes, and a combination of all four genes, i.e. A27L, L1R, A33R and B5R and then challenged with a lethal dose of VACV. The dual and multiple construct vaccinations were performed with gold beads coated with individual constructs. Scarified mice served as a positive control. Two weeks after final vaccination, mice were challenged intraperitoneally (i.p.) with $5\times10^8$ PFU (12.5 $LD_{50}$) of VACV WR.

Figure 10A:
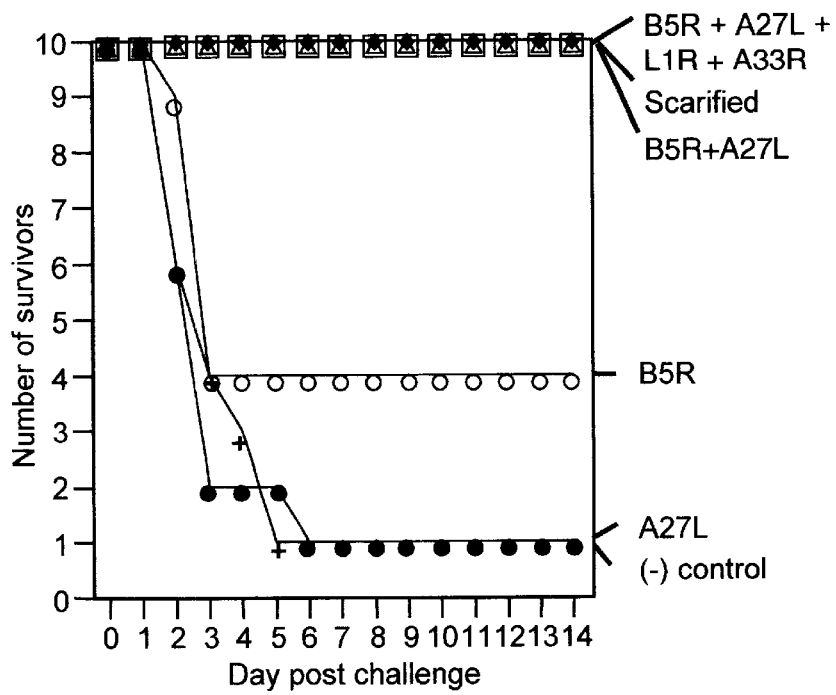
FIGS. 10A and 10B. Protection experiment. Vaccinated animals were challenged i.p. with $5\times10^8$ PFU of VACV WR (12.5 $LD_{50}$). A. The number of survivors each day after challenge are shown. B. Mice were weighed at the indicated day postchallenge and the percentage of starting weight was calculated. B5R+A27L group, closed triangles, B5R+A27L+L1R+A33R group, open squares, Scarified group, closed diamonds, B5R group, open circles, A27L group, cross, negative control, closed circles. For each group, animals with the highest and lowest weight change were excluded from the calculations.
Figure 10B:
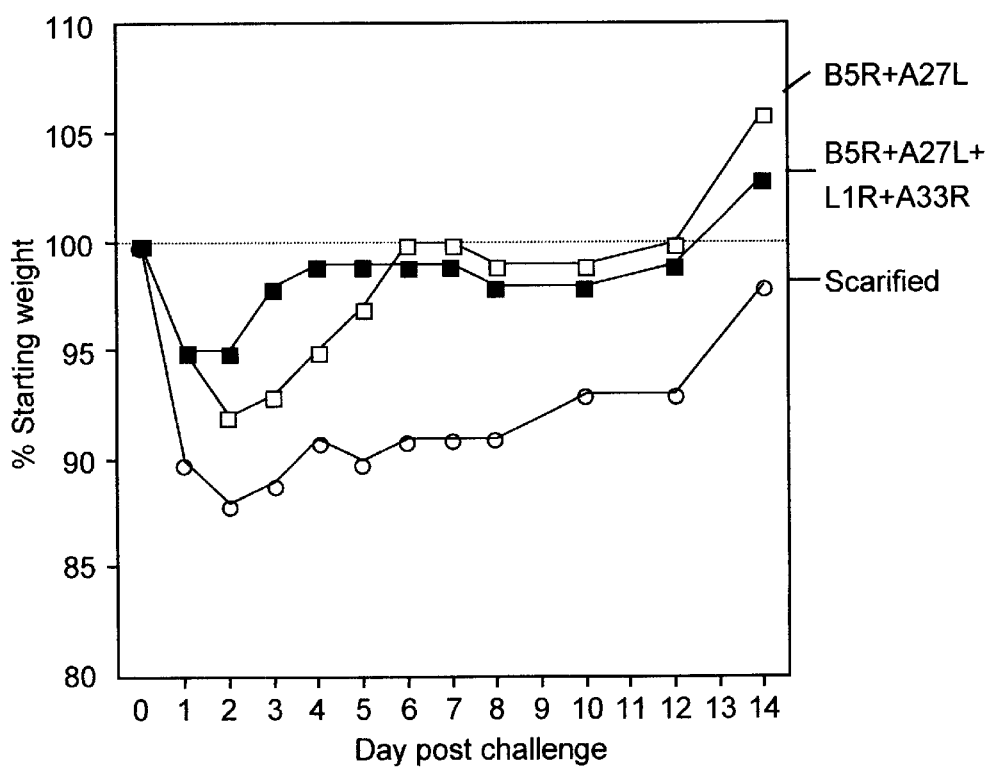

Results indicate that vaccination with A27L elicited neutralizing antibodies, but failed to protect mice from lethal challenge (FIG. 9). Vaccination with B5R elicited a non-neutralizing antibody response, and exhibited little protection. However, when mice were vaccinated with both A27L and B5R, all of the mice were protected. Similarly, mice vaccinated with all 4 genes were completely protected. FIG. 10 shows the kinetics of the lethality of the challenge. The three groups, B5R+A27L, scarified, and B5R+A27L+L1R+A33R were completely protected. Weight loss was monitored after challenge, and the DNA vaccinated groups show less weight loss after challenge than the scarified group (FIG. 11).

TABLE 2

Experimental design and vaccination schedule

| Group | # mice | Immunogen | DNA per cartridge (ug) | Number of cartridges per dose | Boost 1 (wks after priming) | Boost 2 (wks after boost2) | Final Bleed (wks after final boost) |
|---|---|---|---|---|---|---|---|
| 1 | 10 | (−) control[a] | 1 | 2 | 3 | 2 | 2 |
| 2 | 10 | pWRG/B5R | 1 | 2 | 3 | 2 | 2 |
| 3 | 10 | pWRG/A27L | 1 | 2 | 3 | 2 | 2 |
| 4 | 10 | pWRG/B5R + pWRGA27L [different gold] | 1 | 1 each | 3 | 2 | 2 |
| 5 | 10 | pWRG/B5R + pWRGL1R [different gold] | 1 | 1 each | 3 | 2 | 2 |
| 6 | 10 | pWRG/B5R + pWRGA33R [different gold] | 1 | 1 each | 3 | 2 | 2 |
| 7 | 10 | pWRG/A27L + pWRGA33R [different gold] | 1 | 1 each | 3 | 2 | 2 |
| 8 | 10 | pWRG/A27L + pWRG/L1R [different gold] | 1 | 1 each | 3 | 2 | 2 |
| 9 | 10 | pWRG/A27L + pWRG/L1R + pWRG/B5R + pWRG/A33R [different gold] | 1 | 1 each | 3 | 2 | 2 |
| 10 | 10 | Scarification[b] | NA | NA | NA | NA | NA |

Note.
NA, not applicable
[a](−) control, negative control plasmid
[b]VACV (Connaught strain) 10 ul drop of PBS containing 8 × 10[6] PFU scratched into tail ~1 cm from base) as positive controls.
Bleed schedule: for all groups, bleed immediately prior to each vaccination, and just prior to challenge (2 weeks after final boost).

Our results show that DNA vaccination with IMV immunogens L1R or A27L elicits neutralizing antibodies in mice, and DNA vaccinations with EEV immunogens A33R and B5R elicits non-neutralizing antibodies in mice. DNA vaccination with L1R+A27L+A33R+B5R completely protects mice from challenge, and the lack of weight loss indicates low morbidity.

EXAMPLE 6

Protective efficacy in rhesus macaques. Next we tested immunogenicity of the vaccine in rhesus macaques. The gene gun was used to deliver two blasts of each gene, i.e. pWRG/A33R, pWRG/L1R, pWRG/B5R, pWRG/A27L, into the abdominal epidermis. A group of monkeys vaccinated with a live vaccinia virus previously used in humans was used as a control. Monkeys were gene gun-vaccinated 3 times at 2–3 week intervals, and then received a fourth vaccination after 5 weeks. Control monkeys vaccinated with live VACV were vaccinated 2 times 6 weeks apart.

Figure 11A:
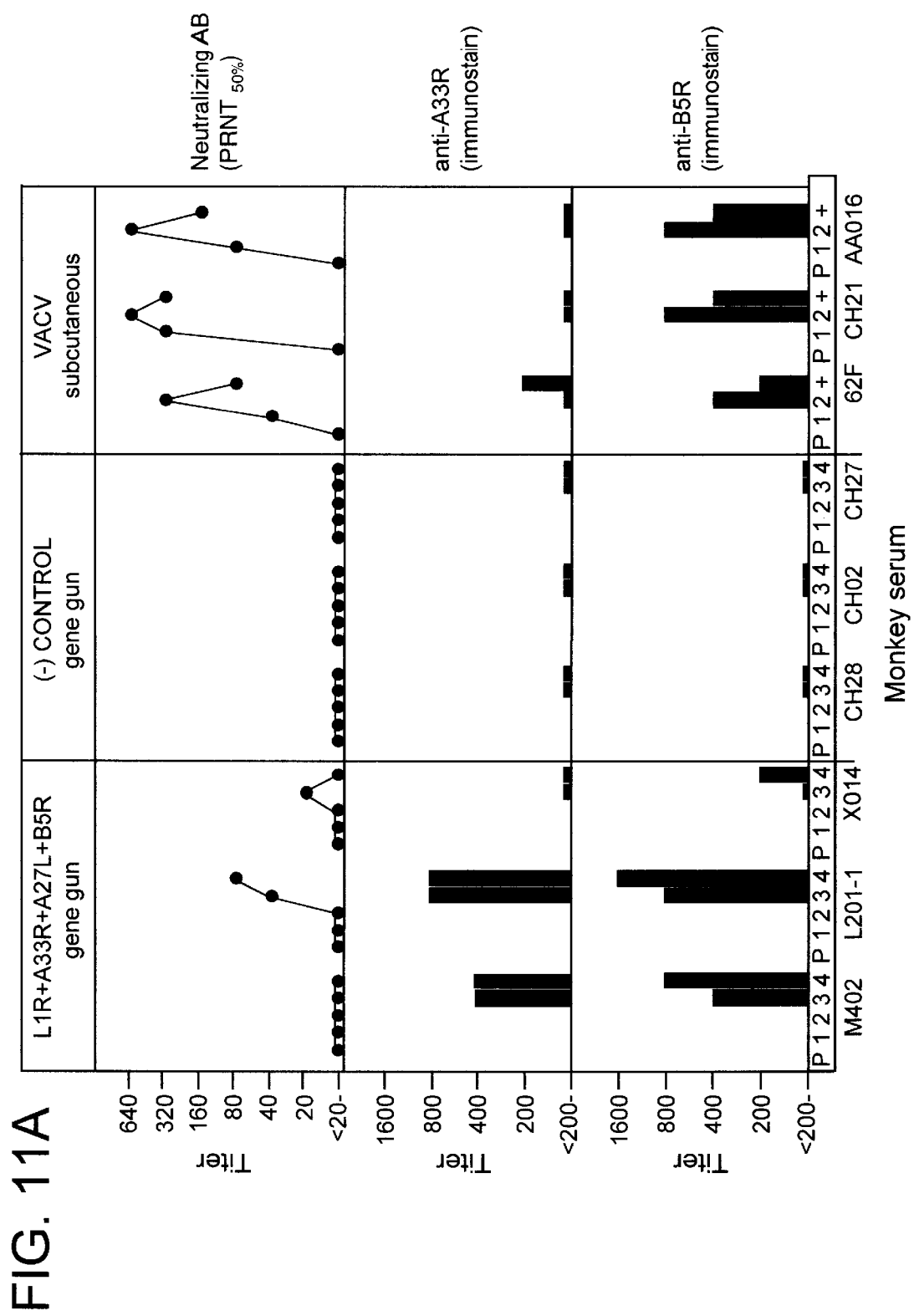
Figure 11B:
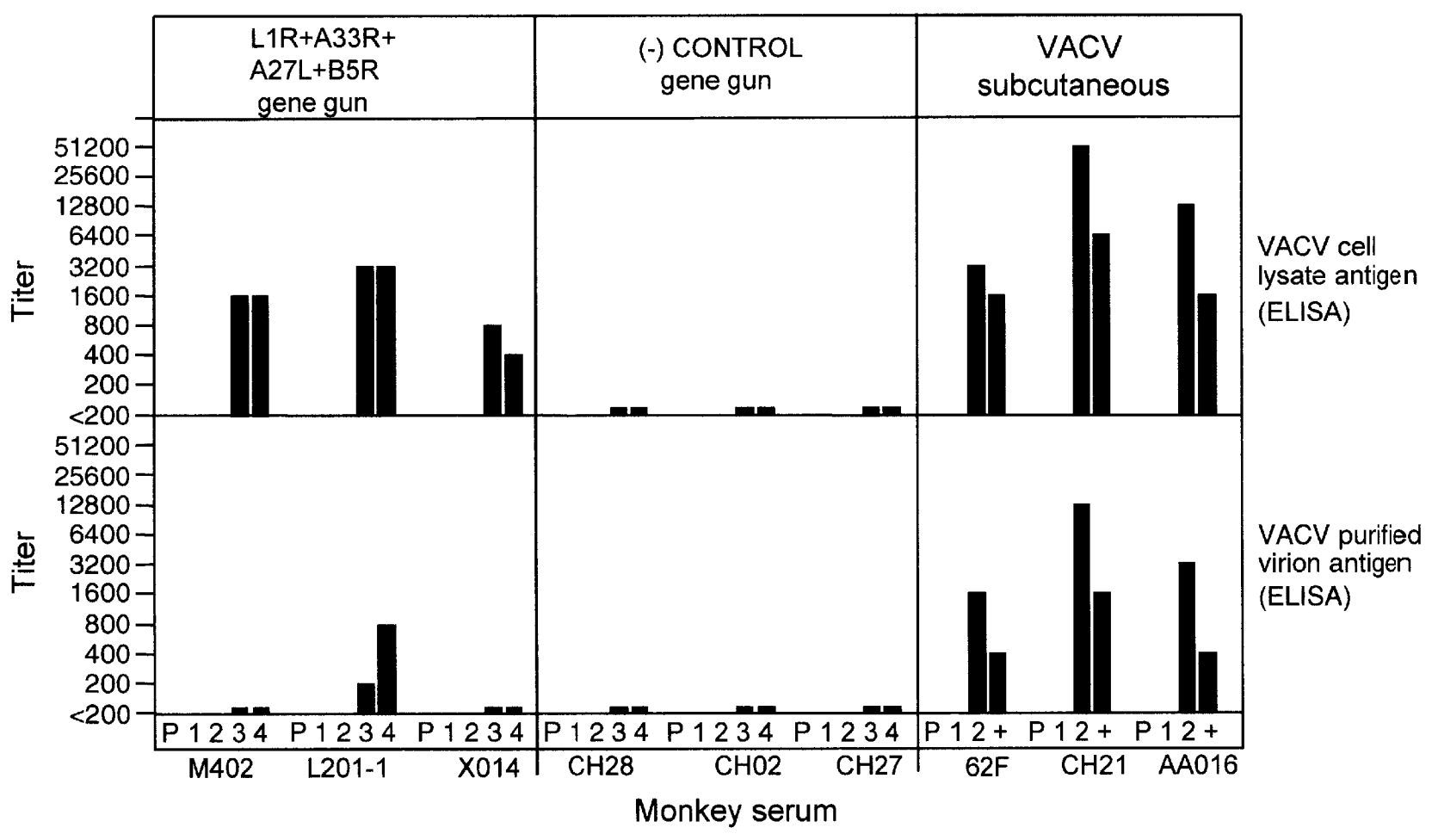

Two gene gun vaccinated monkeys developed a low neutralizing antibody response. Two monkeys developed a good A33R and B5R response that was greater than in the positive control (FIG. 11A). All three gene gun vaccinated monkeys were positive by infected cell lysate ELISA but only one was positive by virion ELISA. (FIG. 11B).

Figure 12A:
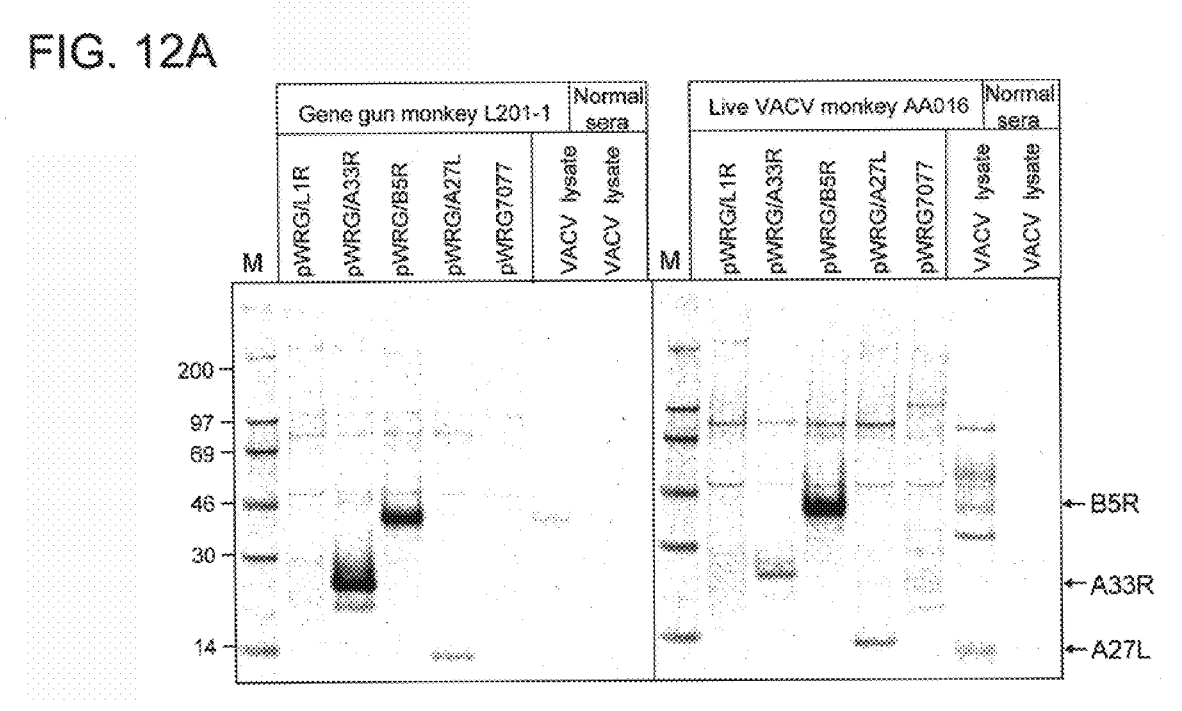

To convince ourselves that the gene gun vaccinated monkeys did, in fact, develop antibody responses to the immunogens, we performed immunoprecipitations. COS cells were transfected with the indicated plasmid, radilabeled after 24 hours, and then combined with the monkey sera (FIG. 12A). The immunoprecipitations proved that the DNA vaccines eleicited antibody responses against A33R, B5R, and A27L. We were unable to detect a L1R response by this method. The response was nearly identical to the response in the live VACV vaccinated monkeys.

Figure 12B:
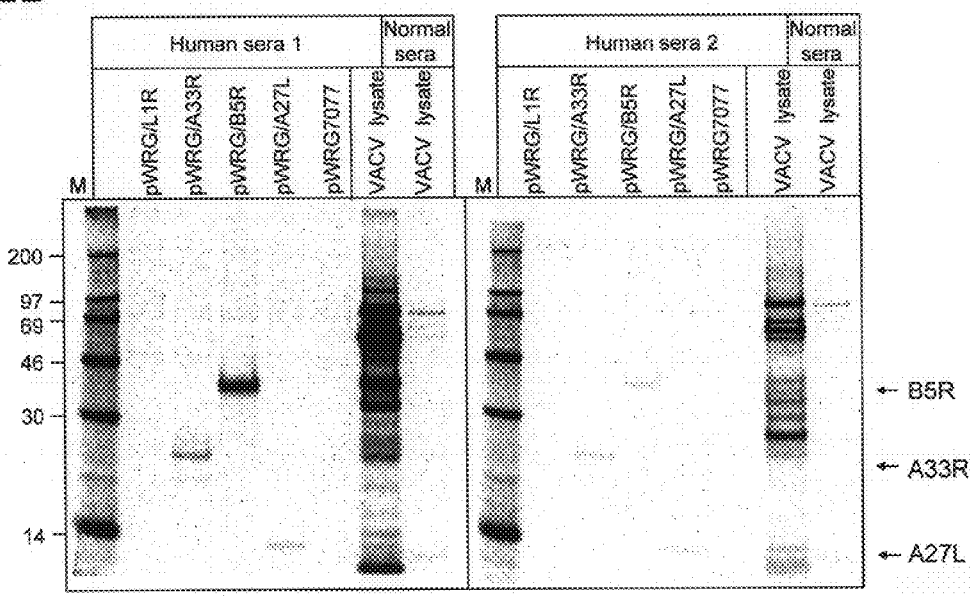

To get an idea of what kind of response the existing smallpox vaccine elicits in humans, we performed immunoprecipitations using sera from recently vaccinated humans. As shown in FIG. 12B, the antibody response to A33R, B5R, and A27L is similar, or weaker, to the response in the gene gun vaccinated monkeys. L1R is difficult to detect by immunoprecipitation.

Human antibody VIG used to treat cases of disseminated vaccinia virus was then used for immunoprecipitations. As shown in FIG. 12C, VIG does contain antibodies to A33R, L1R, B5R, and A27L.

Therefore, our results indicate that DNA vaccination with L1R+A27L+A33R+B5R elicits an antibody response in rhesus monkeys. The neutralizing antibody response is relatively low. The EEV immunogen response is relatively high. Human VIG contains antibodies to L1R, A27L, A33R, and B5R.

Discussion

The smallpox vaccine, i.e., scarification with VACV, is one of the oldest and most successful vaccines ever developed. A sustained worldwide vaccination program resulted in the eradication of naturally occurring smallpox disease in 1979. However, elimination of smallpox has not eliminated the need for a poxvirus vaccine and/or other anti-poxvirus measures such as vaccinia immunglobulin (VIG) because other pathogenic poxviruses (e.g., monkeypox virus) and bioterrorism remain a threat (Breman, 1998. N. Engl. J. Med. 339, 556–559). We are interested in determining if a subset of VACV genes administered as naked DNA constructs could a.) provide protection against poxvirus infection (i.e., replace VACV scarification), and/or b.) serve as immunogen for the generation of protective monoclonal antibodies (i.e., replace VIG).

Of the ~200 genes that comprise the vaccinia genome, only five encode proteins that are known to elicit a neutralizing antibody response including: H3L (Gordon et al., 1991), A27L (Lai et al., 1991; Rodriguez and Esteban 1987), B5R (Galmiche et al., 1999), D8L (Hsiao et al. 1999), and L1R (Ichihashi et al., 1994; Wolffe et al., 1995). Given the structural complexity of VACV, there may be other neutralizing antigens not yet identified. In addition, the A33R gene encodes a protein that elicits a non neutralizing antibody response that is, nevertheless, protective (Schmaljohn unpublished; Galmiche et al., 1999, Virology 254, 71–80). Two core proteins (A10L and A4L) demonstrate some protective immunity; however, it is unclear if the immunity is humoral or cell-mediated (Demkowicz et al., 1992, J. Virol. 66, 386–398). As a first step toward determining if a combination of vaccinia proteins could provide the basis for an alternative poxvirus vaccine or VIG, we evaluated the immunogenicity and protective efficacy of two gene products that are found either on the IMV or EEV.

L1R. Our results show that vaccination with the L1R gene can elicit neutralizing antibodies and provide protection against lethal poxvirus infection. We found that the monospecific neutralizing antibody titers elicited by vaccination with L1R were only twofold lower than the polyclonal neutralizing antibody response generated by tail scarification with VACV. We suspect that modification of our construct or vaccination procedure may allow us to increase the anti-L1R neutralizing antibody titer several fold. This optimism is based on the fact that L1R specific MAbs are extremely potent (PRNT50% titer of MAb-7D11 ascitic fluid is 10–5 g/liter (Wolffe et al., 1995, supra).

The virus used in our challenge experiments was derived from infected cell lysates, and therefore consists primarily of IMV. Because L1R is found on the surface of IMV, it is likely that L1R vaccination confers protection by eliciting neutralizing antibodies that reduce the effective virus challenge well below 1 $LD_{50}$. It remains unclear if anti-L1R antibodies play a role in preventing dissemination of virus from infected cells after establishment of infection. The observation that MAb-7D11 failed to prevent plaque formation in vitro when added to cells after infection (unpublished data) suggests that L1R-specific neutralization involves inhibition of an early step in infection (e.g., attachment or penetration) and not cell-to-cell spread. This is not surprising because the forms of virus most prominent in cell-to-cell spread, CEV and EEV (Payne, 1980, J. Gen. Virol. 50, 89–100), are inaccessible to anti-L1R antibodies, which neutralize the IMV form of virus (Ichihashi et al., 1996, Virology 202, 834–843; Wolffe et al., 1995, supra). It is conceivable that L1R-specific neutralizing antibodies play a role in vivo by neutralizing IMV released from infected cells (by immune mechanisms or by virus-induced cell lysis. We have not investigated the possibility that vaccination with L1R elicits a cell-mediated immune response that contributes to protective immunity.

A33R. Based on our earlier passive protection studies of MAbs specific to A33R, we suspected that vaccination with a naked DNA construct expressing the A33R product might confer protection. The experiments reported here, and those recently reported by others (Galmiche et al., 1999, supra), confirmed that vaccination with the A33R gene does provide some protection against VACV. Galmiche et al. found that vaccination of mice with purified baculovirus expressed A33R protein, or a naked DNA construct expressing A33R, protected against a lethal intranasal (i.n.) VACV (strain IHD-J) challenge (Galmiche et al., 1999, supra). In addition, Galmiche et al. found that passive transfer of serum from A33R vaccinated mice, but not rabbits, could passively protect mice against i.n. challenge. We previously found that A33R-specific monoclonal antibodies (e.g., MAb-1G10) plus complement lysed VACV-infected cells (Schmaljohn, unpublished data). Together these findings suggest that vaccination with A33R elicits antibodies that provide a degree of protection by directing the lysis of VACV-infected cells. In our challenge model, i.p. challenge with VACV WR, vaccination with A33R alone protected some mice in one experiment (Group 3 in FIGS. 4–5); however, only one of 10 mice was protected when A33R was combined with L1R on the same gold beads, and none of the mice vaccinated with A33R combined with a negative control plasmid were protected despite relatively high anti-A33R antibody titers. Also, in a follow-up experiment designed to reexamine the protective efficacy of A33R, all 10 mice vaccinated with pWRG/A33R alone died within 4 days after i.p. challenge. These data suggest that an anti-A33R response fails to confer a consistent level of protection against an i.p. challenge with VACV WR.

It seems likely that an immune response to A33R plays a role principally in reducing the dissemination of virus or the yield of infectious virions per cell, not in preventing primary infection. Failure of vaccination with A33R to consistently protect mice from an i.p. challenge might indicate that 1.) the initial infection is itself lethal, or 2.) levels of disseminating progeny virus produced after challenge with $5 \times 10^8$ PFU overwhelm the anti-A33R immune response. On the other hand, vaccination with A33R may protect against a smaller challenge dose that requires more dissemination for lethality, such as the i.n route of challenge used by Galmiche et al. ($10^{5-6}$ PFU of the IHD-J strain of VACV)(Galmiche et al., 1999, supra).

L1R+A33R[same gold]. Although mice vaccinated with both L1R and A33R on the same gold beads had anti-A33R responses equivalent to those given only A33R, neutralizing antibodies were not detected. To our knowledge, this is the first description of one DNA vaccine immunogen suppressing the antibody response to a co-delivered immunogen. This result was not due to a technical problem in co-loading two plasmid preparations on the same gold beads because both plasmids could be eluted from the cartridges used to vaccinate the mice (data not shown). In addition, this result was not due to A33R- and L1R-specific antibody interaction (e.g., A33R-specific antibodies sterically interfering with binding of L1R-specific antibodies) because mice vaccinated with L1R and A33R on different gold exhibited high titers of both A33R specific antibodies and neutralizing antibodies (presumably L1R specific). Although there was no evidence that A33R affects L1R immunogenicity in VACV-infected cells, it is possible that A33R downregulated translation or processing of L1R in plasmid transfected cells by direct or indirect interactions, and in doing so suppressed L1R immunogenicity. Another possible explanation for our results is that A33R-specific antibodies, elicited during the first vaccination, may have directed lysis of A33R-expressing cells during subsequent boosts and, in doing so, diminished the boosting effect. This hypothesis predicts that immunogens that require boosts to elicit detectable immune responses may be adversely affected by co-delivery of pWRG/A33R. Consistent with this hypothesis, neutralizing antibodies to VACV were not detected after a single vaccination with pWRG/L1R (data not shown), indicating boosts are required for a detectable anti-L1R response. It remains to be determined if pWRG/A33R can inhibit immune responses to other co-delivered immunogens.

L1R+A33R[different gold]. Vaccination with L1R and A33R administered on different gold beads, and therefore delivered to different cells, resulted in a greater level of protection than either immunogen alone. Mice vaccinated with both immunogens appeared to be protected almost as well as the scarified mice. Our working hypothesis is that L1R-specific antibodies limit the initial infection by neutralizing challenge virus (which is predominantly IMV), and A33R-specific antibodies are involved in preventing EEV dissemination by eliminating EEV or infected cells (e.g., via antibody-dependent cell-mediated cytotoxicity or antibody-dependent complement-mediated cytotoxicity). Lysis of infected cells may result in release of IMV and, in the absence of IMV neutralizing antibodies, may allow IMV-mediated dissemination.

The challenge model used here, WR strain of VACV administered to mice by the i.p. route, has been used previously to assess the protective efficacy of vaccination with individual VACV immunogens (Demkowitz et al. 1992). We used this model to demonstrate that vaccination with L1R and A33R provides protection; however, since this is one vaccination protocol, one challenge virus, and one route of challenge, it will be important to evaluate the protective efficacy of these immunogens in other challenge models that use different viruses (e.g., other virulent VACV strains such as the IHD-J strain or other poxviruses such as monkeypox virus), different routes of administration (e.g., i.n. or aerosol routes), or different susceptible animal species (e.g., monkeys). It will also be necessary to optimize vaccine formulations and vaccination schedules.

In summary, in this study we demonstrated that vaccination of mice with VACV genes encoding proteins found on the surface of two infectious forms of the virus (L1R found on the IMV and A33R found on the EEV) provide a greater level of protection than vaccination with either gene alone. By combining additional VACV immunogens with L1R and A33R, it may be possible to develop a vaccine that elicits an even more potent and redundant anti-poxvirus immune response. These studies should also help identify targets for the rational design of a monoclonal antibody-based replacement for VIG.

What is claimed is:

1. A DNA vaccine against poxviruses comprising at least three of the poxvirus nucleic acids selected from the group consisting of: a nucleic acid encoding L1R, a nucleic acid encoding A33R, a nucleic acid encoding A27L, a nucleic acid encoding B5R, a nucleic acid encoding a homolog of L1R, a nucleic acid encoding a homolog of A33R, a nucleic acid encoding a homolog of A27L, and a nucleic acid encoding a homolog of B5R.

2. The DNA vaccine of claim 1 wherein said poxvirus protected against is an Orthopoxvirus chosen from the group consisting of: camelpox virus, ectromelia virus, raccoon poxvirus, skunk poxvirus, Tatera poxvirus, Uasin Gishu virus, Volepox virus, variola virus, vaccinia virus, monkeypox virus, and cowpox virus.

3. The DNA vaccine of claim 1, which comprises a nucleic acid encoding L1R, a nucleic acid encoding A33R, and a nucleic acid encoding A27L.

4. The DNA vaccine of claim 1, which comprises a nucleic acid encoding a homolog of L1R, a nucleic acid encoding a homolog of A33R, and a nucleic acid encoding a homolog of A27L.

5. The DNA vaccine of claim 1, which comprises a nucleic acid encoding L1R, a nucleic acid encoding A33R, and a nucleic acid encoding B5R.

6. The DNA vaccine of claim 1, which comprises a nucleic acid encoding a homolog of L1R, a nucleic acid encoding a homolog of A33R, and a nucleic acid encoding a homolog of B5R.

7. The DNA vaccine of claim 1, which comprises a nucleic acid encoding A27L a nucleic acid encoding A33R, and a nucleic acid encoding B5R.

8. The DNA vaccine of claim 1, which comprises a nucleic acid encoding a homolog of A27L, a nucleic acid encoding a homolog of A33R, and a nucleic acid encoding a homolog of B5R.

9. The DNA vaccine of claim 1, which comprises a nucleic acid encoding L1R, a nucleic acid encoding A27L, and a nucleic acid encoding B5R.

10. The DNA vaccine of claim 1, which comprises a nucleic acid encoding a homolog of L1R, a nucleic acid encoding a homolog of A27L, and a nucleic acid encoding a homolog of B5R.

11. The DNA vaccine of claim 1, which comprises a nucleic acid encoding L1R, a nucleic acid encoding A33R, a nucleic acid encoding A27L, and a nucleic acid encoding B5R.

12. The DNA vaccine of claim 1, which comprises a nucleic acid encoding a homolog of L1R, a nucleic acid encoding a homolog of A33R, a nucleic acid encoding a homolog of A27L, and a nucleic acid encoding a homolog of B5R.

13. A method for inducing in a subject an immune response against poxvirus infection comprising administering to said subject an immunologically effective amount of at least three of the poxvirus nucleic acids selected from the group consisting of: a nucleic acid encoding L1R, a nucleic acid encoding A33R, a nucleic acid encoding A27L, a nucleic acid encoding B5R, a nucleic acid encoding a homolog of L1R, a nucleic acid encoding a homolog of A33R, a nucleic acid encoding a homolog of A27L, and a nucleic acid encoding a homolog of B5R, in an acceptable diluent.

14. A composition of matter comprising at least three carrier particles, each carrier particle having a DNA sequence coated thereon, the DNA sequence comprising a promoter operative in the cells of a mammal and a protein coding region encoding for a poxvirus antigen chosen from the group consisting of: L1R antigen, A33R antigen, A27L antigen, B5R antigen, a homolog of L1R antigen, a homolog of A33R antigen, a homolog of A27L antigen, and a homolog of B5R antigen, wherein the at least three carrier particles each have a DNA sequence coated thereon having a protein coding region encoding for a different poxvirus antigens.

15. A method for inducing a protective immune response to a poxvirus in a mammal, comprising (i) preparing at least three nucleic acid sequences coding for a poxvirus antigen chosen from the group consisting of L1R antigen, A33R antigen, A27L antigen, B5R antigen, a homolog of L1R antigen, a homolog of A33R antigen, a homolog of A27L antigen, and a homolog of B5R antigen, which nucleic acid sequences are each operatively linked to a promoter operative in cells of a mammal;

(ii) coating the nucleic acids in (i) onto carrier particles; and (iii) accelerating the coated carrier particles into epidermal cells of the mammal in vivo.

16. The method according to claim 15 wherein the carrier particles are gold.

17. The method according to claim 15 wherein said poxvirus is an Orthopoxvirus chosen from the group consisting of: camelpox virus, ectromelia virus, raccoon poxvirus, skunk poxvirus, Tatera poxvirus, Uasin Gishu virus, Volepox virus, variola virus, vaccinia virus, monkeypox virus, and cowpox virus.

18. A DNA construct comprising
(i) a vector selected from the group consisting of adenovirus viral vector and Venezuelan equine encephalitis viral vector; and
(ii) at least three of the nucleic acids selected from the group consisting of: a nucleic acid encoding L1R, a nucleic acid encoding A33R, a nucleic acid encoding A27L, a nucleic acid encoding B5R, a nucleic acid encoding a homolog of L1R, a nucleic acid encoding a homolog of A33R, a nucleic acid encoding a homolog of A27L, and a nucleic acid encoding a homolog of B5R.

19. The DNA construct of claim 18, which further comprises a mammalian promoter sequence operably linked to each of the at least three nucleic acids.

* * * * *